United States Patent [19]

Casagrande et al.

[11] Patent Number: 4,673,671

[45] Date of Patent: Jun. 16, 1987

[54] METHOD FOR IMPROVING THE ABSORPTION AND EFFECTIVENESS OF A CATECHOLAMINE COMPOUND

[75] Inventors: Cesare Casagrande, Arese Mi; Francesco Santangelo, Milan, both of Italy

[73] Assignee: SIMES Societa Italiana Medicinali e Sintetici S.p.A., Milan, Italy

[21] Appl. No.: 748,587

[22] Filed: Jun. 25, 1985

[30] Foreign Application Priority Data

Jun. 25, 1984 [IT] Italy ............................ 21583 A/84

[51] Int. Cl.⁴ ...................... A61K 31/675; C07F 9/12
[52] U.S. Cl. ..................................... 514/80; 514/82; 514/114; 540/542; 558/190; 546/25

[58] Field of Search .................. 514/114, 82, 80; 558/190; 540/542; 546/25

[56] References Cited

U.S. PATENT DOCUMENTS 2,944,074 7/1960 Atherton ........................... 558/190
3,914,343 10/1975 Vollmer et al. .................... 558/190
4,322,410 3/1982 Stjepanovic et al. ............... 558/190

Primary Examiner—Anton H. Sutto
Attorney, Agent, or Firm—Berman, Aisenberg & Platt

[57] ABSTRACT

A catecholamine compound is converted to a new mono O-phosphate ester derivative thereof which exhibit improved absorption and effectiveness.

20 Claims, No Drawings

METHOD FOR IMPROVING THE ABSORPTION AND EFFECTIVENESS OF A CATECHOLAMINE COMPOUND

This invention relates to a method for improving the absorption of a catecholamine compound, the compound thus obtained, the pharmaceutically acceptable salts thereof, and the pharmaceutical compositions containing them.

More particularly this invention relates to a method for improving the absorption and therefore effectiveness of a catecholamine compound in a patient exhibiting a syndrome for which the pharmacological action of said catecholamine compound is useful, comprising converting such catecholamine compound to a mono O-phosphate ester derivative thereof, and administering to a patient an effective amount of the resulting mono O-phosphate ester derivative or of a pharmaceutically acceptable salt thereof.

It is known that catecholamine compounds are characterized by the 3,4-dihydroxyphenylethylamine moiety. It is also known that the 3,4-dihydroxyphenylethylamine moiety is common to endogenous catecholamines and to many synthetic compounds as well; this structural feature, which is important for interacting with specific dopaminergic and adrenergic receptors, is a limiting factor for the absorption of these compounds and for the duration of their pharmacological action because it induces quick metabolic inactivations through modifications of the catechol or amino group. The catechol group may be modified by methylation by catechol-O-methyltransferases, or conjugation with sulfuric or glucuronic acid; the amino group, particularly when primary or secondary and without any branching on alpha position of the side-chain may be lost by action the monoamine oxidases.

Endogenous catecholamines are:
1-(3,4-dihydroxyphenyl)-2-amino-ethane or dopamine,
1-(3,4-dihydroxphenyl)-2-methylamino-ethanol or adrenaline, and
1-(3,4-dihydroxyphenyl)-2-amino-ethanol or noradrenaline.

Examples of known pharmacologically active synthetic compounds having catecholamine structure are:
N-isopropyl-2-(3,4-dihydroxyphenyl)-2-hydroxyethylamine,
N-tert.butyl-2-(3,4-dihydroxyphenyl)-2-hydroxyethylamine,
N-ethyl-2-(3,4-dihydroxyphenyl)-2-hydroxy-1-methylamine,
N-isopropyl-2-(3,4-dihydroxyphenyl)-2-hydroxy-1-ethylamine,
1-(3,4,5-trimethoxy-benzyl)-6,7-dihydroxy-1,2,3,4-tetrahydroisoquinoline,
N-methyl-2-(3,4-dihydroxyphenyl)-2-hydroxy-1-methyl-ethylamine,
N-[3-(4-hydroxyphenyl)-1-methylpropyl]-dopamine,
2-(3,4-dihydroxyphenyl)-2-hydroxy-1-methylethylamine,
6,7-dihydroxy-2-amino-1,2,3,4-tetrahydronaphthalene,
5,6-dihydroxy-2-amino-1,2,3,4-tetrahydronaphthalene,
6,7-dihydroxy-2-di-n-propylamine-1,2,3,4-tetrahydronaphthalene,
N,N-di-n-propyldopamine,
N-n-propyl-N-butyldopamine,
2,3,4,5-tetrahydro-6-chloro-7,8-dihydroxy-1-(4-hydroxyphenyl)-1H-3-benzoazepine,
$N^5$-[2-(3,4-dihydroxyphenyl)-ethyl]-L-glutamine,
N-(6-phenethylamino-n-hexyl)-dopamine.

It has now been unexpectedly found that phosphorylation of either phenol hydroxy group of a catecholamine compound improves the absorption and therefore the effectiveness thereof, thus making such compound useful for those therapeutic purposes for which the parent compound has limited usefulness.

Therefore, an object of this invention is a method for improving the absorption and effectiveness of a catecholamine compound in a patient exhibiting a syndrome for which the pharmacological action of said catecholamine compound is useful, said method comprising conversion of such catecholamine compound to a mono O-phosphate ester derivative thereof and administration to a patient of an effective amount of the resulting mono O-phosphate ester derivative of a pharmaceutically acceptable salt thereof.

The phosphorylation step is carried out by reacting an optionally protected catecholamine compound or a precursor thereof (i.e. an appropriate synthetic intermediate), with a suitable phosphorylating agent.

Before or after the phosphorylation step, the hydrogen atom of one hydroxy group of the phosphoric radical may be substituted by a $C_1$–$C_6$ alkyl optionally substituted by one or more hydroxy, alkoxy, acyloxy, amino, carboxy, or alkoxycarbonyl groups; or by a phenyl or a phenylalkyl.

The phosphorylation reaction according to this invention allows converting either phenol hydroxy group of a catecholamine compound to the following group:

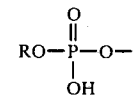

where R is hydrogen, phenyl, phenylalkyl, or a $C_1$–$C_6$ alkyl optionally substituted by hydroxy, alkoxy, acyloxy, amino, carboxy or alkoxycarbonyl.

The phosphorylated derivatives of catecholamine compounds wherein R is different from hydrogen will be indicated hereinbelow as diesters. Therefore the term diester is intended to designate those compounds wherein two hydrogen atoms of the phosphoric moiety have been substituted, it being understood that they are monoesters as far as the catecholamine compound is concerned.

Suitable phosphorylating agents are phosphoric acid and the reactive derivatives thereof. Examples of suitable phosphorylating agents are: orthophosphoric and pyrophosphoric acid, phosphorous pentoxide, polyphosphoric acid, chlorophosphoric acid acids, phosphoryl chloride and bromide; these phosphorylating agents will make it possible to obtain the phosphoric ester directly, even if in some cases it will be necessary to perform a cleavage of P-Cl, P-Br, or P-O-P linkage by adding water to the reaction mixture at the end of the phosphorylation step. Other phosphorylating agents suitable for the introduction of the simple phosphoric group in which R=H but requiring a specific step to remove the protective group are dibenzylphosphorochloridate and diphenylphosphorochloridate from which the benzyl or phenyl groups can be removed by hydrogenolysis, 2-chloro-2-oxo-1,3,2-benzodioxaphosphole, whose protective system can be removed by oxidation, 4,5-dimethyl-2-(1-imidazlyl)-2-oxo-1,3,2- dioxophosphole, and others. A few phosphorylating agents such as for example 2-cyanoethyl dihydrogen phosphate and dibenzyl hydrogen phosphate require the addition of a suitable condensing agent such as N,N-dicyclohexylcarbodiimide.

To obtain diesters in which R is other than hydrogen the phosphorodichloridates of the following formula are useful:

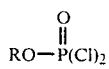

and also the phosphorochloridates of the formula

It is possible to remove not only a chlorine atom but also one of the two R radicals by a hydrolysis step of the respective intermediate products carrying respectively the radical

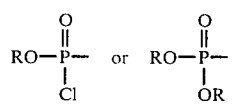

The diester obtained carrying the radical

is considerably more stable than the starting triester and partial selective hydrolysis is thus possible. It is also useful to employ mixed phosphorochloridates of the formula

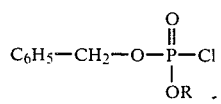

which makes it possible to obtain intermediate triesters from which the benzyl group can be removed by hydrogenolysis. To obtain diesters in which R is other than hydrogen it is also possible to introduce the R radical in an intermediate previously subjected to phosphorylation. For this purpose can be used an intermediate obtained by phosphorylation with phosphoryl chloride or with 4,5-dimethyl-2-(1-imidazolyl)-2-oxo-1,3,2-dioxophosphole or with 4,5-dimethyl-2-chloro-2-oxo-1,3,2-dioxophosphole which is interacted with a molecule of alcohol of the formula ROH. Alternatively, an intermediate diester carrying a benzyl substituent, preferably in the form of one of its alkaline or silver salts, can be alkylated with an RZ' reagent in which Z' is an atom of halogen or an arylsulfonyloxy or alkylsulfonyloxy group, obtaining an intermediate triester from which the desired diester will be obtained by hydrogenolysis of the benzyl group.

The phosphorylation reactions may be carried out in the absence of a solvent, the phosphorylating agent itself acting as a reaction solvent, or in a suitable non reactive solvent such as a hydrocarbon optionally halogenated, an acyclic or cyclic ether, an amide, or a tertiary or heterocylic amine.

Preferred solvents are methylene chloride, tetrahydrofurane, ethyl acetate, dimethylformamide, and pyridine. The reaction is performed at a temperature of from $-80°$ C. to $+100°$ C., depending on the selected phosphorylating agent. It is possible to remove any possible volatile reaction products such as water and hydrochloric acid by operating at reduced pressure and thereby directing the course of the reaction toward the formation of the ester.

In the case of reagents which lead to the formation of acid byproducts it is possible to use suitable acceptors of acids such as the alkaline carbonates and bicarbonates or the tertiary or heterocyclic amines such as triethylamine or pyridine which can themselves be used as reaction solvents. Alternatively it is possible to make a salt of the phenol hydroxy group which it is intended to phosphorylate by treatment with a base such as sodium hydride, sodium methoxide, or potassium tert-butoxide and thus neutralize the acidity generated in the course of the reaction.

The phosphorylation reaction can be carried out directly on the compounds from which it is intended to obtain the phosphorylated derivative or on their derivatives carrying suitable protective groups to direct the phosphorylation selectively, avoiding reactions with other functional groups, in particular with the amino group and above all with the hydroxy group of the catechol group which it is not intended to phosphorylate. It is apparent that phosphorylation of a free catechol system will generally lead (except in the case of derivatives in which the two hydroxy groups of the catechol system have different chemical reactivity) to two phosphorylated isomers which will require appropriate separation procedures.

Similarly, an intermediate compound can be subjected to phosphorylation and is then converted to the desired products by further transformations in other regions of the molecule.

The protective groups (if any can be selected from among those which can be removed under neutral conditions, either moderately acid or basic, without alteration of the phosphoric ester linkage) are those, such as the benzyl, trityl or benzyloxycarbonyl groups, which can be removed by hydrogenolysis; the tert-butyloxycarbonyl, 1-adamantyloxycarbonyl or trityl groups, which can be removed under mild acid conditions; and the trifluoroacetyl, 3-fluorenylmethoxycarbonyl or 1,1-dimethyl-2-cyanoethoxycarbonyl groups, which can be removed under mild basic conditions. Similar protective groups can be present in the phosphorylating ragent, linked both to the other oxygen atoms of the phosphoric group and to substituent present on the R radical, or can be present in the reagent utilized for the introduction of the R radical when it is introduced in a subsequent step. The same group or groups removable under the same conditions will be selected preferably so that all the protective groups can be removed in a single step.

Preferred embodiments of the process according to this invention are as follows:

(a) Compounds, such as N-methyldopamine 3-O-dihydrogen phosphate and N-methyldopamine 4-O-dihydrogen phosphate can be synthesized by direct phosphorylation of the N-methyldopamine with polyphosphoric acid and separation by ion exchange chromatography of the resulting mixture of the two isomers.

(b) The free phenolic hydroxy group on 4-position of the 3-O-benzyl-N-benzyloxycarbonyldopamine is reacted with the dibenzylphosphorochloridate; 3-O-benzyl-N-benzyloxycarbonyldopamine 4-O-dibenzyl-phosphate is obtained and subjected to catalytic hydrogenation which simultaneously removes all the protective groups, thus obtaining dopamine 4-O-dihydrogen phosphate. In addition to the monoester phosphates it is also possible to synthesize diester phosphate with the above-described methods. (c) Phosphorylation with phosphoryl chloride of a free hydroxy group on 4-position of the 3-O-benzyl N-benzyloxycarbonyl-N-methyldopamine leads to the formation of a phosphorodichloridate whose reaction with one equivalent of ethanol followed by hydrolyzation in water leads to 3-O-benzyl-N-benzyloxycarbonyl-N-methyldopamine 4-O-ethyl hydrogen phosphate. The same product is obtained by condensation of the phenol hydroxy group with ethylphosphorodichloridate and subsequent hydrolyzation of the thus formed ethylphosphorochloridate. Alternatively, condensation of the 3-O-benzyloxycarbonyl-N-methyoldopamine with diethylphosphochloridate gives 3-O-benzyl-N-benzyloxycarbonyl-N-methyldopamine 4-O-diethylphosphate which is converted into 4-O-ethyl hydrogen phosphate by partial hydrolyzation.

N-methyldopamine 4-O-hydrogen phosphate is obtained from the 3-O-benzyl-N-benzyloxycarbonyl-N-methyldopamine 4-O-ethyl-hydrogen phosphate prepared by one of the three methods described above after catalytic hydrogenation. (a) The 3-hydroxy-4-benzyloxy-alpha-tert.butylamino-acetophenone is first phosphorylated with the dibenzylphosphorochloridate and subsequently subjected to catalytic hydrogenation which simultaneously reduces the carbonyl to a hydroxy group and removes all the groups present obtaining thus N-tert-butyl-2-(3,4-dihydroxyphenyl)-2-hydroxyethylamine 3-O-dihydrogen phosphate. (b) The hydroxy group on 6-position of the 5,6-dihydroxy-1,2,3,4-tetrahydro-1-naphthalenone is selectively benzylated while the remaining hydroxy group on 5-position is protected by a different group to yield the 5-methoxymethoxy-6-benzyloxy-1,2,3,4-tetrahydro-1-naphthalenone. By reaction of the latter with dimethylsulfonium methylide, an intermediate epoxide is obtained which by reaction with di-n-propylamine yields 5-methoxy-methoxy-6-benzyloxy-1-(di-n-propylaminomethyl)-1-hydroxy-1,2,3,4-tetrahydronaphthalene. The hydroxy group on 5-position is selectively deprotected and can thus react with the dibenzylphosphorochloridate. In this manner 1,5,6-trihydroxy-1-(di-n-propylaminomethyl)-1,2,3,4-tetrahydronaphthalene 5-O-dibenzylphosphate is obtained. After catalytic hydrogenation under acid conditions which simultaneously removes the hydroxy group and all the protective groups 5,6-dihydroxy-1-(di-n-propylamino-methyl)-1,2,3,4-tetrahyronaphthalene 5-O-dihydrogenphosphate is obtained.

Alternatively, synthesis pathways (construction of the ethylamine chain, cyclizations, introduction of substituents) can be used starting from previously phosphorylated intermediates. Thus 3-O-benzyldopamine 4-O-dibenzylphosphate is reacted with styrene oxide to give N-(1-hydroxy-2-phenyl-ethyl)-3-O-benzyldopamine 4-O-dibenzyl phosphate which is cyclized under acid conditions to give 7-benzyloxy-8-hydroxy-1-phenyl-2,3,4-5-tetrahydro-1H-3-benzazepine 8-O-dibenzylphosphate from which the protective groups are removed by catalytic hydrogenation thus obtaining 7,8-dihydroxy-1-phenyl-2,3,4,5-tetrahydro-1H-benzozepine 8-O-dihydrogen phosphate.

Another object of this invention is a catecholamine compound wherein a phenol hydroxy group of the catechol moiety has been converted to the group

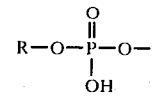

where R has the above mentioned meanings and the pharmaceutically acceptable salts thereof.

A preferred embodiment of this invention is a compound of formula:

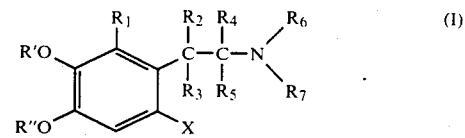 (I)

wherein R' is hydrogen when R" is

and is

when R" is hydrogen, R is hydrogen, phenyl, phenylalkyl, or a $C_1$–$C_6$ alkyl optionally substituted by hydroxy, alkoxy, acyloxy, amino, carboxy or alkoxycarbonyl;

$R_1$ is hydrogen, halogen, alkyl, alkoxy or together with $R_3$, $R_5$ or $R_7$ has the meanings indicated below;

X is hydrogen or together with $R_3$, $R_5$ or $R_7$ has the meanings indicated below;

$R_2$ is hydrogen or hydroxy;

$R_3$ is hydrogen or together with $R_1$ or X forms a ring having from 5 t 8 members;

$R_4$ is hydrogen or alkyl;

$R_5$ is hydrogen, alkyl or together with $R_1$ or X forms a ring having from 5 to 8 members;

$R_6$ is hydrogen, allyl, an acyl group of a natural acid, or a $C_1$–$C_6$ alkyl optionally substituted by phenyl, 4-hydroxyphenyl, or a phenylalkylamino group, having from 1 to 3 Carbon atoms in the alkyl moiety;

$R_7$ is hydrogen, a $C_1$–$C_6$ alkyl or together with $R_1$ or X forms a ring having from 5 to 8 members.

When not otherwise specified the radicals which constitute the meanings of the substituents in the general formula I are preferably:

alkyl=straight or branched $C_1$–$C_4$ alkyl, alkoxy=$C_1$–$C_4$ alkoxy, acyloxy=alkylcarbonyloxy having from 1 to 4 carbon atoms in the alkyl moiety, alkoxycarbonyl=alkoxycarbonyl having from 1 to 4 carbon atoms in the alkoxy moiety, phenylalkyl=a phenylalkyl group having from 1 to 4 carbon atoms in the alkyl moiety,
halogen=fluorine, chlorine, bromine, or iodine.

Preferred meanings of the various substituents in formula I are: for R, hydrogen, a $C_1$-$C_4$ alkyl optionally substituted by $C_1$-$C_4$ alkoxy and acyloxy where the acyl group is in turn an alkylcarbonyl having from 1 to 4 carbon atoms in the alkyl moiety; for $R_1$, hydrogen, halogen and together with $R_3$, $R_5$ or $R_7$ the meanings indicated below; for X, hydrogen and together with $R_3$, $R_5$ or $R_7$ the meanings indicated below; for $R_2$, hydrogen and hydroxy; for $R_3$, hydrogen, and together with $R_1$ or X trimethylene; for $R_4$, hydrogen and methyl; for $R_5$, hydrogen and together with $R_1$ or X ethylene; for $R_6$, hydrogen, glutamyl, a $C_1$-$C_6$ alkyl optionally substituted by hydroxyphenyl, or by a phenyl alkylamino group having from 1 to 3 carbon atoms in the alkyl moiety; for $R_7$, hydrogen, $C_1$-$C_4$ alkyl and together with $R_1$ or X methylene, $CH_2O$, and ethylene optionally substituted by phenyl, hydroxyphenyl or trimethoxybenzyl.

Preferred compounds of this invention are: dopamine 4-O-dihydrogen-phosphate, dopamine 3-O-dihydrogenphosphate, N-methyldopamine 4-O-dihydrogenphosphate, N-methyldopamine 3-O-dihydrogenphosphate, adrenaline 3-O-dihydrogenphosphate, adrenaline 4-O-dihydrogenphosphate, 7,8-dihydroxy-1-phenyl-2,3,4,5-tetrahydro-1H-benzoazepine 7-O-dihydrogen phosphate, 7,8-dihydroxy-1-phenyl-2,3,4,5-tetrahydro-1H-3-benzoazepine 8-O-dihydrogen phosphate, N-methyldopamine 4-O-ethyl hydrogenphosphate, N-methyldopamina 3-O-(2-methoxy)ethyl hydrogenphosphate, N-methyldopamine 3-O-pivaloyloxymethyl hydrogenphosphate, N,N-di-n-propyldopamine 4-O-dihydrogenphosphate, N-tert.butylamino-2-(3,4-dihydroxyphenyl)-2-hydroxy-ethylamine 3-O-dihydrogenphosphate, N[3-(4-hydroxyphenyl)-1-methylpropyl]-dopamine 4-O-dihydrogenphosphate, 1-(3,4,5-trimethoxybenzyl)-6,7-dihydroxy-1,2,3,4-tetrahydroisoquinoline 7-O-dihydrogenphosphate, $N^5$-[2-(3,4-dihydroxyphenyl)-ethyl]L-glutamine, dopamine 4-O-ethyl-hydrogenphosphate, 7,8-dihydroxy-1-(4-hydroxyphenyl)-2,3,4,5-tetrahydro-1H-3-benzoazepine 8-O-dihydrogenphosphate, $N^5$-[2-[3-hydroxy-4-(ethyl-hydrogenphosphonoxy)-phenyl]-ethyl]-L-glutamine methylester 4-O-dihydrogen phosphate, N-(3,4-dihydroxyphenylethyl)-N'-(2-phenylethyl)-hexane-1,6-diamine 4-O-dihydrogenphosphate, N-[3-(4-hydroxyphenyl)-1-methylpropyl]-dopamine 4-O-ethyl-hydrogen-phosphate, 7,8-dihydroxy-6-chloro-1-(4-hydroxyphenyl)-2,3,4,5-tetrahydro-1H-3-benzoazepine 8-O-dihydrogenphosphate, N-(3,4-dihydroxyphenylethyl)-N'-(2-phenylethyl)hexane-1,6-diamine 4-O-ethyl-hydrogenphosphate, 1-(N,N-di-n-propylaminomethyl)-5,6-di-hydroxy-1,2,3,4-tetrahydro-1-naphthalene 5-O-dihydrogenphosphate, and 1-(N,N-di-n-propylaminomethyl)-5,6-dihydroxy-1,2,3,4-tetrahydro-1-naphthalene 6-O-dihydrogenphosphate.

Because of the possible presence in the structure of the compounds of this invention of asymmetrical carbon atoms (e.g. when $R_3$=H and $R_2$=OH) and other structural elements which cause the presence of isomeric forms the compounds of this invention can also occur as mixtures of optical and/or geometrical isomers. The mixture of isomers as well as the individual optical and geometrical isomers obtained by separation of the isomers or by stereoselective or stereospecific synthesis are included in the scope of the present invention.

Another object of the present invention are the salts of the compounds of this invention with nontoxic organic and inorganic acids or bases suitable for pharmaceutical use.

Pharmaceutically acceptable addition salt of this invention include those formed with hydrochloric, hydrobromic, sulfuric, phosphoric, acetic, citric, maleic, lactic, ascorbic, and methansulfonic acids, as well as with sodium, potassium, magnesium, calcium, diethylamine, ethanolamine, trihydroxymethylaminomethane, lysine, glucamine, and arginine.

The compounds of this invention and their pharmaceutically acceptable salts show favourable absorption and increased effectiveness in known assay systems allowing evaluation of the effects on dopaminergic and adrenergic receptors responsive to pharmacologically active catecholamine compounds. Therefore they can be advantageously used in the therapy of cardiovascular and renal diseases, such as congestive heart failure, acute and chronic renal failure and hypertension; in the therapy of bronchial asthma, and in ophthalmological therapy for reducing intraocular pressure.

The activity of N-methyldopamine 4-O-dihydrogenphosphate on cardiovascular parameters in anesthetized dogs was compared with that of N-methyldopamine; both compounds were administered by intraduodenal route. The results are shown in the following table.

TABLE

Maximum percentage variations of renal blood flow and resistances obtained in anesthetized dogs by i.d. administration of N—methyldopamine 4-0-dihydrogenphosphate and N—methyldopamine hydrochloride.

| | | N—methyldopamine 4-0-dihydrogenphosphate | | | | N—methyldopamine HCl |
|---|---|---|---|---|---|---|
| Dose (kg i.d). | mmoles | 0.005 | 0.01 | 0.02 | 0.04 | 0.035 |
| | mg | 1.25 | 2.5 | 5 | 10 | 7.1 |
| | Renal blood flow | +14.2% | +18.5%** | +36.4%** | +31.7%** | +14.9% |
| | renal vascular resistances | −11.2% | −14.1% | −24.5%* | −28.1%** | −14% |
| No. of experiments | | 6 | 6 | 7 | 7 | 5 |

(Statistical significance *P <0.05 **P <0.01)

N-methyldopamine 4-O-dihydrogenphosphate showed an improved absorption and a long-lasting renal vasodilating action (about four hours) without any modification of other hemodynamic parameters whereas N-methyldopamine showed a smaller effect for two hours although administered in higher doses. In addition the effects of N-methyldopamine were accompanied by an undesired increase of blood pressure and by stimulation of the heart. Thus N-methyldopamine 4-O dihydrogenphosphate showed improved effectiveness, either in terms of activity or duration of action or selective renal vasodilating action. These properties are useful in the therapy of heart failure, hypertension, and renal failure.

Similarly, a marked increase of renal blood flow (+46%) and reduction of renal resistances (−32%) were induced by N-methyldopamine 4-O-ethyl-hydrogenphosphate at a dose of 5 mg/kg (0.018 mmoles/kg) and by N-methyldopamine 4-O-methyl-hydrogen phosphate (+26%, −19%, at a dose of 5 mg/kg=0.019 mmole/kg, respectively). The effects of these compound lasted over 5 hours.

Dopamine 4-O-dihydrogenphosphate (5 mg/kg, 0.02 mmoles/kg) and N-gamma-glutamyldopamine 4-O-dihydrogen phosphate (5 mg/kg, 0.014 mmoles/kg) also induced selective and long lasting increase (+14.5 and +25%) in renal blood flow and decrease (−15 and −18%) in renal resistances, while dopamine was ineffective at a dose of 10 mg/kg (0.053 mmoles/kg).

N-methyldopamine 3-O-dihydrogenphosphate and 4-O-dihydrogen phosphate also increased urine excretion in normally hydrated rats when administered orally at 0.29 mmoles/kg; the observed increases was 180% and 170% ($p < 0.05$), respectively, while N-methyldopamine was ineffective at the same dose. These diuretic properties are useful in the therapy of hypertension and cardiac and renal failure.

N,N-di-n-propyldopamine 4-O-dihydrogenphosphate reduced blood pressure by 30-35% ($p < 0.01$) when orally administered to spontaneous hypertensive rats at a dose of 0.29 mmoles/kg; the effect lasted five hours while N,N-di-n-propyl dopamine was ineffective at the same dosage and also at 0.58 mmoles/kg.

The improved absorption of the compound of this invention has been observed not only by appropriate pharmacological assays, such as those described above, but also by pharmacokinetic assays, using specific and sensitive analytical methods, such as high pressure liquid chromatography with electrochemical detector allowing the determination of very low concentrations of catecholamine compounds in body fluids, e.g., 1 ng/ml. Preferred conditions include working at 100 atm on a C18 HS 3 Perkin Elmer column, (internal diameter: 4.6 mm; length: 100–200 mm) filled with silica gel chemically linked to C-18-hydrocarbon chains and using as mobile phase a flow of about 1 ml/min. of a mixture of the following solvents in variable ratios from 96:4 to 70:30.

(a) 100 mM formic acid, containing 1 mM citric acid, 0.4 mM n-octane sulphonic acid, 0.1 mM ethylendiaminetetraacetic acid and 0.25% diethylamine, and adjusted to pH 3 with potassium hydroxide.
(b) acetonitrile The electrochemical detector is equipped with a working electrode of glassy carbon and a reference electrode of silver/silver cyanide and is operated between 0.6 and 0.9 V.

For practical applications in therapy the compounds of this invention and their pharmaceutically acceptable salts can be administered as they are, but they are preferably administered in the form of pharmaceutical compositions.

Said compositions are another object of the present invention and contain as their active ingredient one or more compounds of this invention or their salts with nontoxic organic or inorganic acids or bases suitable for pharmaceutical use together with liquid or solid pharmaceutical excipients suitable for systemic administration as oral, peroral, rectal, and parenteral administration or topical, such as aerosol or ophthalmic administration.

In the case of parenteral administration peculiar advantages are offered by the improved duration and selectivity of action.

The pharmaceutical compositions can be in solid form as tablets, pills, capsules, slow release forms or in liquid form as solutions, suspensions or emulsions.

In addition to the usual excipients, the compositions may contain additives suitable for pharmaceutical use as preservatives, stabilizers, emulsifiers, salts for regulating osmotic pressure, buffers, flavouring and colouring agents.

If particular therapies require it is possible to associate in the compositions which are the object of this invention other compatible active ingredients whose concomitant administration is therapeutically useful.

For practical uses in therapy the amount of the compound of this invention to be administered may vary over a rather broad range depending on known factors, such as the specific therapy required, the pharmaceutical composition, the administration way, and the effectiveness of the specific compound of this invention which is used.

The pharmaceutical compositions can be made following the conventional techniques of the pharmaceutical chemist involving mixing, granulating and compressing when necessary, or variously mixing and dissolving the ingredients as appropriate to give the desired end product.

In general the daily dosage of the compounds of this invention will range from 0.01 to 10 mg//kg and will be administered in one or more doses at appropriate intervals.

For the purpose of better illustrating the invention the following examples are now given:

EXAMPLE 1

A solution of 40 g of N-benzyloxycarbonyldopamine, 35.19 g of benzyl chloride, and 105.8 g of NaHCO₃ in 400 ml of absolute ethanol was refluxed under stirring for 7 hours.

After filtration the filtrate was evaporated to dryness, redissolved in ethyl acetate, washed with $H_2O$, dried over $Na_2SO_4$, and evaporated to dryness. The residue was chromatographed on a silica gel column (eluent, $CH_2Cl_2$) eluting in sequence the 3,4-O-dibenzyl-N-benzylcarbonyldopamine (m.p. 73°–75° C. from hexane), the 3-O-benzyl-N-benzyloxycarbonyldopamie (m.p. 93°–95° C. from ethyl ether), and the 4-O-benzyl-N-benzyloxycarbonyldopamine (m.p. 124°–126° C. from 95% ethanol).

EXAMPLE 2

697 mg of NaH were added under nitrogen to 10 g of 3-O-benzyl-N-benzyloxycarbonyldopamine obtained as described in example 1 and dissolved in 100 ml of dimethylformamide.

After an hour at room temperature the reaction mixture was cooled to 5° C. and a solution of 8.6 g of dibenzylphosphorochloridate into 100 ml of toluene was added dropwise.

After 30 minutes the reaction mixture was poured into water and extracted with ethyl ether, the organic extract was dried over $Na_2SO_4$ and evaporated. The residue was purified by chromatography on a silica gel column (eluent, $CH_2Cl_2$/ethyl acetate=9/1) obtaining 3-O-benzyl-N-benzyloxycarbonyldopamine 4-O-dibenzylphosphate as chromatographically pure oil (T.L.C., eluent: toluene/ethyl acetate=6/4, detection by UV light 240 nm and/or $I_2$ vapours).

EXAMPLE 3

To 11 g of 3-O-benzyl-N-benzyloxycarbonyldopamine 4-O-dibenzylphosphate obtained as described in example 2 dissolved in 500 ml of 80% aqueous ethanol were added 2.2 g of 10% Pd/C catalyst and hydrogenated at room temperature under a hydrogen pressure of 2–3 atm.

When the theoretical absorption of hydrogen was over the reaction mixture was filtered, the ethanol filtrate discarded and the solid product was separated from the catalyst, by dissolution with warm water and filtration of the catalyst. The aqueous solution was concentrated to a small volume and diluted with ethanol. The dopamine 4-O-dihydrogenphosphate was thus obtained by crystallization, m.p. 210°–220° C. (from water).

EXAMPLE 4

Proceeding as described in example 2 but replacing for the 3-O-benzyl-N-benzyloxycarbonyldopamine an equivalent quantity of 4-O-benzyl-N-benzyloxycarbonyldopamine obtained as described in example 1, 4-O-benzyl-N-benzyloxycarbonyldopamine 3-O-dibenzylphosphate was obtained as chromatographically pure oil (T.L.C. eluent, toluene/ethyl acetate=6:4, UV, $I_2$ detection).

EXAMPLE 5

Proceeding as in example 3 but replacing for the 3-O-benzyl-N-benzyloxycarbonyldopamine 4-O-dibenzylphosphate an equivalent quantity of 4-O-benzyl-N-benzyloxycarbonyldopamine 3-O-dibenzylphosphate obtained as described in example 4, dopamine 3-O-dihydrogenphosphate was obtained, m.p. 210°–225° C. (from ethanol/water).

EXAMPLE 6

Proceeding as in example 2 but replacing for the 3-O-benzyl-N-benzyloxycarbonyldopamine an equivalent quantity of 3-O-benzyl-N-benzyloxycarbonyl-N-methyldopamine, 3-O-benzyl-N-benzyloxycarbonyl-N-methyldopamine 4-O-dibenzylphosphate was obtained as chromatographically pure oil (T.L.C., eluent: $CH_2Cl_2$/ethyl acetate=9/1, UV, $I_2$ detection).

The 3-O-benzyl-N-benzyloxycarbonyl-N-methyldopamine in turn was obtained from the N-benzyloxycarbonyl-N-methyldopamine proceeding in a manner similar to that described in example 1 for the N-benzyloxycarbonyldopamine, m.p. 63°–65° C. (from ethyl acetate/petroleum ether b.p. 30°–70° C.).

EXAMPLE 7

Proceeding as in example 3 but replacing for the 3-O-benzyl-N-benzyloxycarbonyldopamine 4-O-dibenzylphosphate an equivalent quantity of 3-O-benzyl-N-benzyloxycarbonyl-N-methyldopamine 4-O-dibenzylphosphate obtained as described in example 6, N-methyldopamine 4-O-dihydrogenphosphate was obtained, m.p. 205°–208° C. (from ethanol/water).

EXAMPLE 8

Proceeding as in example 2 but replacing for the 3-O-benzyl-N-benzyloxycarbonyldopamine an equivalent quantity of 4-O-benzyl-N-benzyloxycarbonyl-N-methyldopamine, 4-O-benzyl-N-benzyloxycarbonyl-N-methyldopamine 3-O-dibenzylphosphate was obtained as chromatographically pure oil (T.L.C., eluent: methylene chloride/ethyl acetate=9/1, UV, $I_2$ detection). The 4-O-benzyl-N-benzyloxycarbonyl-N-methyldopamine was in turn obtained from the N-benzyloxycarbonyl-N-methyldopamine, proceeding an a manner similar to that described in example 1 for the N-benzyloxycarbonyldopamine, m.p. 105°–106° C. (from ethyl acetate/petroleum ether b.p. 30°–70° C.).

EXAMPLE 9

Proceeding as in example 3 but replacing for the 3-O-benzyl-N-benzyloxycarbonyldopamine 4-O-dibenzylphosphate an equivalent quantity of 4-O-benzyl-N-benzyloxycarbonyl-N-methyldopamine 3-O-dibenzylphosphate obtained as described in example 8, N-methyldopamine 3-O-dihydrogenphosphate was obtained, m.p. 201°–203° C. (from ethanol/water).

EXAMPLE 10

To a solution of 180 g of alpha-(N-benzyloxycarbonyl-N-methylamino)-3,4-dihydroxyacetophenone, and 72 g of benzyl chloride in 2.5 l of absolute ethanol was added under reflux a solution of sodium ethylate in ethanol prepared from 13 g of sodium in 400 ml of absolute ethanol. The reaction mixture was refluxed for four hours, the hot mixture was then filtered to remove the sodium chloride, the solution was allowed to stand overnight at room temperature and filtered to collect the crystalline alpha-(N-benzyloxycarbonyl-N-methylamino)-3-hydroxy-4-benzyloxyacetophenone, m.p. 141°–143° C. (from ethanol). The mother waters were evaporated and the residue was dissolved in 1N sodium hydroxide, extracted with methylene chloride and then made acid with hydrochloric acid. The unreacted alpha-(benzyloxycarbonyl-N-methylamine)-3,4-dihydroxyacetophenone which can be recycled was thus recovered.

EXAMPLE 11

Proceeding as in example 2 but replacing for the 3-O-benzyl-N-benzyloxycarbonyldopamine an equivalent quantity of alpha-(N-benzyloxycarbonyl-N-methylamino)-3-hydroxy-4-benzyloxyacetophenone obtained as described in example 10, alpha-(N-benzyloxycarbonyl-N-methylamino)-3-hydroxy-4-benzyloxyacetophenone 3-O-di-benzylphosphate was obtained as chromatographically pure oil (T.L.C., eluent: toluene/ethyl acetate=6/4, UV, $I_2$ detection).

EXAMPLE 12

To a solution of 144 g of alpha-(N-benzyloxycarbonyl-N-methylamino)-3-hydroxy-4-benzyloxyacetophenone 3-O-dibenzylphosphate obtained as described in example 11 were added 12.25 g of $NaBH_4$. After 30 minutes at room temperature the reaction mixture was made acid with 1N hydrochloric acid, concentrated to one-half volume, diluted with water, and extracted with methylene chloride.

The organic layer was dried over sodium sulfate and evaporated to dryness. The residue was purified by chromatography on a silica gel column (eluent: methylene chloride/ethyl acetate=9/1) obtaining 4-O-benzyloxycarbonyladrenaline 3-O-dibenzylphosphate as chromatographically pure oil (T.L.C., eluent: toluene-/ethyl acetate=6/4, UV, $I_2$ detection).

EXAMPLE 13

Proceeding as in example 3 but replacing for the 3-O-benzyl-N-benzyloxycarbonyldopamine 4-O-dibenzylphosphate an equivalent quantity of 4-O-benzyl-N-benzyloxycarbonyladrenaline 3-O-dibenzylphosphate obtained as described in example 12, adrenaline 3-O-dihydrogenphosphate was obtained, m.p. 160°–162° C. (from ethanol/water).

EXAMPLE 14

To 35 g of 4-O-benzyl-N-benzyloxycarbonyladrenaline 3-O-dibenzylphosphate (obtained as described in example 12) dissolved in 350 ml of pyridine were added at room temperature 35 ml of acetic anhydride. After 7 hours the reaction mixture was concentrated under reduced pressure. The residue was dissolved in ethyl acetate and washed with dilute hydrochloric acid, a solution of sodium bicarbonate and then water. The organic layer is dried over $Na_2SO_4$, filtered and evaporated under reduced pressure thus obtaining N-benzyloxycarbonyl-N-methyl-2-(3-hydroxy-4-benzyloxyphenyl)-2-acetoxyethylamine 3-O-dibenzylphosphate as chromatographically pure oil (T.L.C., eluent: toluene-/ethyl acetate=6/4, UV, $I_2$ detection).

EXAMPLE 15

Proceeding as in example 3 but replacing for the 3-O-benzyl-N-benzyloxycarbonyldopamine 4-O-dibenzylphosphate an equivalent quantity of N-benzyloxycarbonyl-N-methyl-2-(3-hydroxy-4-benzyloxy-phenyl)-2-acetoxyethylamine 3-O-dibenzylphosphate obtained as described in example 14 and extending hydrogenation time to 7 hours, N-methyldopamine 3-O-dihydrogenphosphate was obtained, m.p. 201°–203° C. (from ethanol/water).

EXAMPLE 16

To a solution of 256 g of alpha-(N-benzyloxycarbonyl-N-methyamino)-3,4-dihydroxyacetophenone in 1 liter of dimethylformamide were added 39 g of sodium hydride at 0° C.
After 3 hours at 0° C. 103 g of benzyl chloride were added and the reaction mixture was maintained at a temperature between 0° C. and 5° C. for 24 hours. The reaction mixture was then poured into water, 150 g of sodium borate were added to solubilize the unreacted starting product, and the solution was extracted first with ethyl acetate and then with methylene chloride.
The organic phases were combined and evaporated and the residue was purified by chromatography on a silica gel column eluting with methylene chloride obtaining thus alpha-(N-benzyloxycarbonyl-N-methylamino)-4-hydroxy-3-benzyloxyacetophenone, m.p. 101°–102° C. (from ethyl acetate).

EXAMPLE 17

Proceeding as in example 2 but replacing for 3-O-benzyl-N-benzyloxycarbonyldopamine an equivalent quantity of alpha-(N-benzyloxycarbonyl-N-methylamino)-4-hydroxy-3-benzyloxyacetophenone obtained as described in example 16, alpha-(N-benzyloxycarbonyl-N-methylamine)-4-hydroxy-3-benzyloxyacetophenone 4-O-dibenzylphosphate was obtained as chromatographically pure oil (T.L.C., eluent: toluene/ethyl acetate=6/4, UV, $I_2$ detection).

EXAMPLE 18

Proceeding as in example 12 but replacing for the alpha-(N-benzyloxycarbonyl-N-methylamine)-3-hydroxy-4-benzyloxyacetophenone 3-O-dibenzylphosphate an equivalent quantity of alpha-(N-benzyloxycarbonyl-N-methylamino)-4-hydroxy-3-benzyloxyacetophenone 4-O-dibenzylphosphate obtained as described in example 17, 3-O-benzyl-N-benzyloxycarbonyladrenaline 4-O-dibenzylphosphate was obtained as chromatographically pure oil (T.L.C., eluent: toluene/ethyl acetate=6/4, UV, $I_2$ detection).

EXAMPLE 19

Proceeding as in example 3 but replacing for the 3-O-benzyl-N-benzyloxycarbonyldopamine 4-O-dibenzylphosphate an equivalent quantity of 3-O-benzyl-N-benzyloxycarbonyladrenaline 4-O-dibenzylphosphate obtained as described in example 18, adrenaline 4-O-dihydrogenphosphate was obtained, m.p. 188°–191° C. (from ethanol/water=8/2).

EXAMPLE 20

Proceeding as in example 14 but replacing for the 4-O-benzyl-N-benzyloxycarbonyladrenaline 3-O-dibenzylphosphate an equivalent quantity of 3-O-benzyl-N-benzyloxycarboyladrenaline 4-O-dibenzylphosphate obtained as described in example 18, N-benzyloxycarbonyl-N-methyl-2-(4-hydroxy-3-benzyloxyphenyl)-2-acetoxyethylamine 4-O-dibenzylphosphate was obtained as chromatographically pure oil (T.L.C., eluent: toluene/ethyl acetate=6/4, UV, $I_2$ detection).

EXAMPLE 21

Proceeding as in example 3 but replacing for the 3-O-benzyl-N-benzyloxycarbonyldopamine 4-O-dibenzylphosphate an equivalent quantity of N-benzyloxycarbonyl-N-methyl-2-(4-hydroxy-3-benzyloxyphenyl)-2-acetoxyethylamine 4-O-dibenzylphosphate obtained as described in example 20 and extending the reaction time to 24 hours, N-methyldopamine 4-O-dihydrogenphosphate was obtained, m.p. 205°–208° C. (from ethanol/water).

EXAMPLE 22

In 150 g of polyphosphoric acid (prepared from 84.8 g of 85% phosphoric acid and 65.2 g of $P_2O_5$ heated for one hour at 80° C. under a nitrogen atmosphere) were dissolved 50 g of N-methyldopamine hydrochloride and the reaction mixture was maintained under stirring for 8 hours at 80° C., then 50 ml of water were added and the reaction mixture was allowed to react for 20 minutes more.
The reaction mixture was diluted first with 250 ml of n-butanol and then with ethyl ether until precipitation of a white solid which, after having been first suspended in ethanol and filtered, was chromatographed on IRA 400 quaternary ammonium ion exchange resin in $^-OH$ form eluting with increasing solutions of ammonium acetate (from 0.01M to 0.08M). At first N-methyl-dopamine 3-O-dihydrogenphosphate was eluted and then N-methyldopamine 4-O-dihydrogenphosphate which were purified by evaporation to dryness at reduced pressure of the respective chromatographic fractions, taking up the residue with water, again evaporating and then crystallyzing the residue from water/ethanol, m.p. 201°–203° C. (from water) and 205°–208° C. (from water) respectively.

EXAMPLE 23

Proceeding as in example 22 but replacing for the N-methyldopamine an equivalent quantity of 7,8-dihydroxy-1-phenyl-2,3,4,5-tetrahydro-1H-3-benzazepine, the two isomeric phosphates 7,8-dihydroxy-1-phenyl-2,3,4,5-tetrahydro-1H-3-benzazepine 7-O and 8-O-dihydrogenphosphate were obtained and were separated by chromatography on IRA 400 ion exchange resin.

EXAMPLE 24

A solution of 3,3 g of N-benzyloxycarbonyl-N-methyl-2-(4-hydroxy-3-benzyloxyphenyl)-2-acetoxyethylamine 4-O-dibenzylphosphate obtained as described in example 20 and of 2.8 g of sodium iodide in 30 ml of acetone was maintained under stirring overnight. The reaction mixture was evaporated and the residue was dissolved in ethyl acetate, washed with water, dried over sodium sulfate and evaporated, thus obtaining N-benzyloxycarbonyl-N-methyl-2-(4-hydroxy-3-benzyloxyphenyl)-2-acetoxyethylamine 4-O-benzyl hydrogenphosphate as chromatographically pure oil (T.L.C., eluent: n-butanol/acetone/acetic acid/water/toluene=1/1/1/1/1, UV, $I_2$ detection).

EXAMPLE 25

A solution of 3.1 g of N-benzyloxycarbonyl-N-methyl-2-(4-hydroxy-3-benzyloxyphenyl)-2-acetoxyethylamine 4-O-benzyl-hydrogenphosphate obtained as described in example 24, 0.84 g of sodium bicarbonate, and 1.31 g of dimethyl sulphate in 50 ml of acetone was refluxed for 4 hours. The reaction mixture was evaporated, the residue was redissolved in ethyl acetate, washed with water, dried over sodium sulfate, evaporated and the residue was purified by chromatography on a silica gel column (eluent: methylene chloride) obtaining N-benzyloxycarbonyl-N-methyl-2-(4-hydroxy-3-benzyloxyphenyl)-2-acetoxyethylamine 4-O-methylbenzylphosphate as chromatographically pure oil (T.L.C., eluent: toluene/ethyl acetate=6/4, UV, $I_2$ detection).

EXAMPLE 26

Proceeding as in example 3 but replacing for the 3-O-benzyl-N-benzyloxycarbonyldopamine 4-O-dibenzylphosphate an equivalent quantity of N-benzyloxycarbonyl-N-methyl-2-(4-hydroxy-3-benzyloxyphenyl)-2-acetoxyethylamine 4-O-methyl-benzylphosphate obtained as described in example 25, N-methyldopamine 4-O-methylhydrogenphosphate was obtained, m.p. 184°–185° C. (from ethanol).

EXAMPLE 27

To a solution of 11.6 g of 3-O-benzyl-N-benzyloxycarbonyl-N-methyldopamine in 120 ml of dimethylformamide, 0.8 g of sodium hydride under nitrogen atmosphere were added.

After 45 minutes at room temperature the reaction mixture was cooled to 5° C. and a solution of 5.62 g of diethylphosphorochloridate in 20 ml of dimethylformamide was added dropwise. After 1 hour at room temperature the reaction mixture was poured in water and extracted with ethyl ether. The extract was washed with water, dried over sodium sulfate and evaporated obtaining 3-O-benzyloxycarbonyl-N-methyldopamine 4-O-diethylphosphate as chromatographically pure oil (T.L.C., eluent: ethyl acetate, UV, $I_2$ detection).

EXAMPLE 28

A solution of 10 g of 3-O-benzyl-N-benzyloxycarbonyl-N-methyldopamine 4-O-diethylphosphate obtained as described in example 27 and 4 g of triethylbenzylammonium bromide in 50 ml of acetonitrile was refluxed for 48 hours. The reaction mixture was evaporated to dryness, taken up with 5% sulfuric acid and extracted with chloroform. The organic phase was washed with water, dried over sodium sulfate and evaporated. The residue was purified by chromatography on a silica gel column (eluent: methylene chloride with increasing quantities up to 10% of methanol). 3-O-benzyl-N-benzyloxycarbonyl-N-methyldopamine 4-O-ethylhydrogenphosphate was obtained thus m.p. 95°–97° C. (from ethanol/ethyl ether).

EXAMPLE 29

To 3.8 g of $POCl_3$ in 150 ml of tetrahydrofurane was added at −60° C. and under nitrogen atmosphere a solution containing the sodium salt of 3-O-benzyl-N-benzyloxycarbonyl-N-methyldopamine obtained by reacting 10 g of 3-O-benzyl-N-benzyloxycarbonyl-N-methyldopamine with 0.65 g of sodium hydride in 150 ml of tetrahydrofurane.

After 2 hours at −60° C. the temperature was allowed to rise to −20° C. and a solution of 1.1 g of absolute ethanol and of 1.9 g of pyridine in 2 ml of tetrahydrofurane was added slowly. After 4 hours at −20° C. the temperature was allowed to rise to 20° C. and were added 50 ml of water with 2 ml of pyridine. After another hour, the reaction mixture was evaporated to dryness, taken up with 0.01N hydrochloric acid and extracted with ethyl acetate. The combined organic phases were dried over sodium sulfate, evaporated, and the residue was purified by chromatography on a silica gel column, eluting with methylene chloride/methanol=9/1, and subsequently was crystallized from ethanol/ethyl ether, thus obtaining 3-O-benzyl-N-benzyloxycarbonyl-N-methyldopamine 4-O-ethylhydrogenphosphate, m.p. 95°–97° C.

EXAMPLE 30

In a nitrogen atmosphere at −60° C. to a solution of 12.2 g of ethylphosphorodichloridate in 100 ml of tetrahydrofurane was added in one hour a solution of tetrahydrofurane containing the sodium salt of the 3-O-benzyl-N-benzyloxycarbonyl-N-methyldopamine prepared by reacting 10 g of the base at room temperature with 0.6 g of sodium hydride in 100 ml of tetrahydrofurane. After 1 hour at −60° C. the temperature is allowed to rise to room temperature and were added 200 ml of water containing 12.8 g of pyridine. After 90 minutes the tetrahydrofurane was evaporated and the residue was extracted with ethyl acetate. The combined organic phase was washed with water, dried over sodium sulfate and evaporated. The residue was crystallized from ethanol/ethyl ether obtaining 3-O-benzyl-N-benzyloxycarbonyl-N-methyldopamine 4-O-ethylhydrogenphosphate, m.p. 95°–97° C.

EXAMPLE 31

Proceeding as in example 3 but replacing for the 3-O-benzyl-N-benzyloxycarbonyldopamine 4-O-dibenzylphosphate an equivalent quantity of 3-O-benzyl-N-benzyloxycarbonyl-N-methyldopamine 4-O-ethyl-hydrogenphosphate obtained as described in examples 28, 29, 30, N-methyldopamine 4-O-ethyl-hydrogenphosphate was obtained, m.p. 184°-187° C. (from ethanol).

EXAMPLE 32

Proceeding as in example 30 but replacing for the ethylphosphorochloridate and for the sodium salt of the 3-O-benzyl-N-benzyloxycarbonyl-N-methyldopamine an equivalent quantity of 2-methoxyethylphosphorodichloridate and the sodium salt of 4-O-benzyl-N-benzyloxycarbonyl-N-methyldopamine, 4-O-benzyl-N-benzyloxycarbonyl-N-methyldopamine 3-O-(2-methyloxyethyl)-hydrogenphosphate was obtained, m.p. 88°-92° C. (from ethyl ether).

EXAMPLE 33

Proceeding as in example 3 but replacing for the 3-O-benzyl-N-benzyloxycarbonyldopamine 4-O-dibenzylphosphate an equivalent quantity of 4-O-benzyl-N-benzyloxycarbonyl-N-methyldopamine 3-O-(2-methoxyethyl)-hydrogenphosphate obtained as described in example 32, N-methyldopamine 3-O-(2-methoxyethyl)-hydrogenphosphate was obtained, m.p. 143°-146° C. (from ethanol).

EXAMPLE 34

A solution of 20 g of 4-O-benzyl-N-benzyloxycarbonyl-N-methyldopamine 3-O-dibenzylphosphate obtained as described in example 8, 27 g of sodium iodide in 300 ml of acetone was maintained under stirring for 24 hours at 20° C.

The reaction mixture was evaporated to dryness and the residue was dissolved in water, acidified with hydrochloric acid and extracted with ethyl acetate. The combined organic layers were dried over sodium sulfate, filtered and evaporated. 4-O-benzyl-N-benzyloxycarbonyl-N-methyldopamine 3-O-benzyl-hydrogenphosphate was thus obtained, m.p. 93°-95° C. (from ethyl ether).

EXAMPLE 35

A solution of 8 g of 4-O-benzyl-N-benzyloxycarbonyl-N-methyldopamine 3-O-benzyl-hydrogenphosphate obtained as described in example 34, 5.55 g of iodomethylpivalate, and 2.35 g of anhydrous potassium carbonate in 80 ml of acetone was refluxed for 14 hours. The reaction mixture was evaporated to dryness and the residue was dissolved in water, made acid with hydrochloric acid and extracted with ethyl acetate. The organic phase was dried over sodium sulfate and evaporated to dryness. The residue was purified by chromatography on a silica gel column eluting with methylene chloride with increasing quantities up to 10% of methanol, 4-O-benzyl-N-benzyloxycarbonyl-N-methyldopamine 3-O-pivaloyloxymethyl-benzylphosphate in chromatographically pure oily form (T.L.C., eluent: methylene chloride/methanol=8/2, UV, $I_2$ detection) was thus obtained.

EXAMPLE 36

Proceeding as in example 3 but replacing for the 3-O-benzyl-N-benzyloxycarbonyldopamine 4-O-dibenzylphosphate an equivalent quantity of 4-O-benzyl-N-benzyloxycarbonyl-N-methyldopamine 3-O-pivaloyloxymethyl-benzylphosphate obtained as described in example 35, N-methyldopamine 3-O-pivaloyloxymethyl-hydrogenphosphate was obtained, m.p. 73°-78° C. (from ethyl ether).

EXAMPLE 37

To a solution of 33.5 g of 3-benzyloxy-4-hydroxyacetophenone in 350 ml of tetrahydrofurane were added slowly at 0°-5° C. 57 g of phenyltrimethylammonium perbromide in 200 ml of tetrahydrofurane. After one night at room temperature were added 10 ml of a 5% solution of sodium bisulfite. The reaction mixture was evaporated to dryness and the residue was dissolved in methylene chloride, washed with water, dried over sodium sulfate and evaporated obtaining 3-benzyloxy-4-hydroxy-alpha-bromoacetophenone in the form of an oil. This product examined with thin-layer chromatography (eluent: toluene/ethyl acetate=8/2, UV, $I_2$ detection) proved to contain a certain quantity (5-20%) of the starting product but it had adequate quality for subsequent reaction with amines, such as for example di-n-propylamine.

EXAMPLE 38

To a solution of 45 g of 3-benzyloxy-4-hydroxy-alpha-bromoacetophenone (obtained as described in example 37) in 150 ml of tetrahydrofurane were added 96 ml of di-n-propylamine. After 30 minutes the reaction mixture was evaporated, the residue was dissolved in ethyl ether, washed with water, dried over sodium sulfate and evaporated. The residue was dissolved in absolute ethyl alcohol, acidified with hydrochloric acid and evaporated. The residue was crystallized from isopropyl alcohol, thus obtaining 3-benzyloxy-4-hydroxy-alpha-di-n-propylaminoacetophenone hydrochloride, m.p. 150°-152° C.

EXAMPLE 39

Proceeding as in example 2 but replacing for the 3-O-benzyl-N-benzyloxycarbonyldopamine an equivalent quantity of 3-benzyloxy-4-hydroxy-alpha-di-n-propylaminoacetophenone hydrochloride obtained as described in example 38, 3-benzyloxy-4-hydroxyalpha-di-n-propylaminoacetophenone 4-O-dibenzylphosphate in chromatographically pure oily form (T.L.C., eluent: methylene chloride/toluene/methyl alcohol=25/5/3, UV, $I_2$ detection) was obtained.

EXAMPLE 40

Proceeding as in example 12 but replacing for the alpha-(N-benzyloxycarbonyl-N-methylamino)-3-hydroxy-4-benzyloxyacetophenone 3-O-dibenzylphosphate an equivalent quantity of 3-benzyloxy-4-hydroxy-alpha-di-n-propylaminoacetophenone 4-O-dibenzylphosphate obtained as described in example 39, N,N-di-n-propyl-2-(4-hydroxy-3-benzyloxyphenyl)-2-hydroxyethylamine 4-O-dibenzylphosphate in chromatographically pure oily form (T.L.C., eluent: methylene chloride toluene/methanol=25/5/3, UV, $I_2$ detection) was obtained.

EXAMPLE 41

Proceeding as in example 14 but replacing for the 4-O-benzyl-N-benzyloxycarbonyladrenaline 3-O-dibenzylphosphate an equivalent quantity of N,N-di-n-propyl-2-(4-hydroxy-3-benzyloxyphenyl-2-hydroxyethylamine 4-O-dibenzylphosphate obtained as described in example 40, N,N-di-n-propyl-2-(4-hydroxy-3-benzyloxyphenyl)-2-acetoxyethylamine 4-O-dibenzylphosphate in chromatographically pure oily form (T.L.C., eluent: methylene chloride/toluene/methanol=25/5/3, UV, I₂ detection) was obtained.

EXAMPLE 42

Proceeding as in example 3 but replacing for the 3-O-benzyl-N-benzyloxycarbonyldopamine 4-O-dibenzylphosphate an equivalent quantity of N,N-di-n-propyl-2-(4-hydroxy-3-benzyloxyphenyl)-2-acetoxyethylamine 4-O-dibenzylphosphate (obtained as described in example 41) and using as solvent 50% aqueous ethanol, N,N-di-n-propyldopamine 4-O-dihydrogenphosphate was obtained, m.p. 220°–227° C. (from water).

EXAMPLE 43

To a solution of 67 g of 4-benzyloxy-3-hydroxyacetophenone in 700 ml of tetrahydrofurane were added slowly at −20° C. 115 g of phenyltrimethylammonium perbromide in 300 ml of tetrahydrofurane. The temperature was allowed to rise to room temperature. The reaction mixture was maintained under stirring for 2 hours and then evaporated to dryness, the residue was diluted with water and extracted with methylene chloride, dried over sodium sulfate, filtered, evaporated and the residue was crystallized from methanol, obtaining 4-benzyloxy-3-hydroxy-alpha-bromoacetophenone, m.p. 139°–141° C.

EXAMPLE 44

To 150 ml of tert.butylamine were added in 30 minutes 45.5 g of 4-benzyloxy-3-hydroxy-alpha-bromoacetophenone obtained as described in example 43. After another 30 minutes the tert-butylamine hydrobromide was separated by filtration. The filtrate was evaporated to dryness under reduced pressure, the residue was dissolved in ethanol and acidified with hydrochloric acid in ethanol. This solution was evaporated and the residue was crystallized from acetone, obtained 3-hydroxy-4-benzyloxy-alpha-tert-butylaminoacetophenone hydrochloride, m.p. 195°–200° C.

EXAMPLE 45

Proceeding as in example 2 but replacing for the 3-O-benzyl-N-benzyloxycarbonyldopamine an equivalent quantity of 3-hydroxy-4-benzyloxy-alpha-tert-butylaminoacetophenone hydrochloride obtained as described in example 44, 3-hydroxy-4-benzyloxy-alph-tert.butylaminoacetophenone 3-O-dibenzylphosphate in chromatographically pure oily form (T.L.C., eluent: methylene chloride/toluene/methanol/conc. ammonium hydroxide=120/30/28/2, UV, I₂ detection) was obtained.

EXAMPLE 46

Proceeding as in example 3 but replacing for the 3-O-benzyl-N-benzyloxycarbonyldopamine 4-O-dibenzylphosphate an equivalent quantity of 3-hydroxy-4-benzyloxy-alpha-tert-butylaminoacetophenone 3-O-dibenzylphosphate obtained as described in example 45, N-tert-butylamino-2-(3,4-dihydroxyphenyl)-2-hydroxyethylamine 3-O-dihydrogenphosphate was obtained, m.p. 180°–190° C. (from water).

EXAMPLE 47

23 g of 3-O-benzyl-4-O-methoxymethyldopamine base obtained as described in example 66, 20.4 g of 4-(4-benzyloxyphenyl)-butan-2-one and 300 mg of p-toluenesulfonic acid in 400 ml of toluene were refluxed for 10 hours while the water was removed azeotropically.

The reaction mixture was evaporated to dryness. The residue was dissolved in 400 ml of methanol, after addition of 4 g of sodium borohydride the reaction mixture was stirred for 2 hours. Afterwards the mixture was evaporated, the residue was dissolved in methylene chloride, washed with water, dried over sodium sulfate, and evaporated to dryness. The residue was dissolved in ethyl ether and 4 g of maleic acid in acetone were added. A crystalline precipitate of 3-O-benzyl-4-O-methoxymethyl-N-3-(4-benzyloxyphenyl)-1-methylpropyl]dopamine maleate was obtained, m.p. 129°–131° C.

EXAMPLE 48

A solution of 19 g of 3-O-benzyl-4-O-methoxymethyl-N-[3-(4-benzyloxyphenyl)-1-methylpropyl]dopamine base (obtained from the corresponding maleate described in example 47 by suspension in water, neutralization with ammonium hydroxide and extraction with chloroform of the base, drying of the solution over sodium sulfate and evaporation to dryness), and 2.7 ml of concentrate hydrochloric acid in 200 ml of methanol was refluxed for 30 minutes. The reaction mixture was concentrated to a small volume, diluted with methylene chloride, washed with diluted ammonia and with water, dried over sodium sulfate and evaporated. The residue was dissolved in acetone, acidified with hydrochloric acid and diluted with ethyl ether. From the solution crystallized 3-O-benzyl-N-[3-(4-benzyloxyphenyl)-1-methylpropyl]dopamine hydrochloride, m.p. 138°–140° C.

EXAMPLE 49

Proceeding as in example 2 but replacing for the 3-O-benzyl-N-benzyloxycarbonyldopamine an equivalent quantity of 3-O-benyl-N-[3-(4-benzyloxyphenyl)-1-methylpropyl]dopamine obtained as described in example 48, 3-O-benzyl-N-[3-(4-benzyloxyphenyl)-1-methylpropyl]dopamine 4-O-dibenzylphosphate in chromatographically pure oily form (T.L.C., eluent: methylene chloride/methanol/toluene=25/3/5, UV, I₂ detection) was obtained.

EXAMPLE 50

Proceeding as in example 3 but replacing for the 3-O-benzyl-N-benzyloxycarbonyldopamine 4-O-dibenzylphosphate an equivalent quantity of 3-O-benzyl-N-[3-(4-benzyloxyphenyl)-1-methylpropyl]dopamine 4-O-dibenzylphosphate obtained as described in example 49, N-[3-(4-hydroxyphenyl)-1-methylpropyl]dopamine 4-O-dihydrogenphosphate was obtained, m.p. 257°–259° C.

EXAMPLE 51

To a mixture of 13.7 g (34 mmoles) of 3-O-benzyl-4-O-methoxymethyldopamine base obtained as described in example 66, 18.7 g of potassium carbonate, 200 ml of chloroform and 130 ml of water were added at 5° C. while stirring 10.8 g of 3,4,5-trimethoxyphenylacetyl chloride in 50 ml of toluene. After 1 hour at room temperature the organic phase was separated, washed with water and evaporated. N-[2-(3-benzyloxy-4-methoxymethoxyphenylethyl]-3,4,5-trimethoxyphenylacetamide was obtained, m.p. 73°–74° C. (from ethyl acetate/hexane).

EXAMPLE 52

A solution of 20 g of N-[2-(3-benzyloxy-4-methoxymethoxyphenylethyl]-3,4,5-trimethoxyphenylacetamide obtained as described in example 51, and 0.5 ml of concentrate hydrochloric acid in 200 ml of methanol was refluxed for 45 minutes. The reaction mixture was evaporated to dryness and the residue was crystallized from acetonitrile. N-[2-(3-benzyloxy-4-hydroxyphenylethyl]-3,4,5-trimethoxyphenylacetamide was obtained, m.p. 139°–141° C.

EXAMPLE 53

A solution of 15 g of N-[2-(3-benzyloxy-4-hydroxyphenylethyl]-3,4,5-trimethoxyphenylacetamide obtained as described in example 52 and 10.6 g of phosphorus oxychloride in 200 ml of acetonitrile was refluxed for 40 minutes. The reaction mixture was evaporated to dryness, and the residue was dissolved in methylene chloride, washed with 5% sodium bicarbonate and with water, dried over sodium sulfate and evaporated. The residue was dissolved in methanol and 2.5 g of sodium borohydride were added. After 30 minutes the solution was evaporated to dryness, and the residue was taken up with methylene chloride, washed with water, dried over sodium sulfate and evaporated. The residue was dissolved in ethanol and to this solution was added ethanol acidified with hydrochloric acid. The mixture was evaporated to dryness and the residue was crystallized from acetone. 1-(3,4,5-trimethoxybenzyl)-7-hydroxy-6-benzyloxy-1,2,3,4-tetrahydroisoquinoline hydrochloride was thus obtained, m.p. 179°–181° C.

EXAMPLE 54

Proceeding as in example 2 but replacing for the 3-O-benzyl-N-benzyloxycarbonyldopamine an equivalent quantity of 1-(3,4,5-trimethoxybenzyl)-7-hydroxy-6-benzyloxy-1,2,3,4-tetrahydroisoquinoline base (obtained from the corresponding hydrochloride obtained as described in example 53, by suspension in water, neutralization with ammonium hydroxide and extraction with chloroform of the base, drying of the solution over sodium sulfate and evaporation to dryness), 1-(3,4,5-trimethoxybenzyl)-7-hydroxy-6-benzyloxy-1,2,3,4-tetrahydroisoquinoline 7-O-dibenzylphosphate in chromatographically pure oily form (T.L.C., eluent: methylene chloride/methanol/concentrate ammonium hydroxide=92/7.5/0.5, UV, $I_2$ detection) was obtained.

EXAMPLE 55

Proceeding as in example 3 but replacing for the 3-O-benzyl-N-benzyloxycarbonyldopamine 4-O-dibenzylphosphate an equivalent quantity of 1-(3,4,5-trimethoxybenzyl)-7-hydroxy-6-benzyloxy-1,2,3,4-tetrahydroisoquinoline 7-O-dibenzylphosphate obtained as described in example 54, 1-(3,4,5-trimethoxybenzyl)-6,7-dihydroxy-1,2,3,4-tetrahydroisoquinoline 7-O-dihydrogenphosphate was obtained, m.p. 209°–212° C. (from water/ethanol=1/1).

EXAMPLE 56

A solution of 9 g of 3-O-benzyl-4-O-methoxymethyldopamine base obtained as described in example 66, 9.23 g of N-benzyloxycarbonyl-L-glutamic acid alpha-methylester, 7.75 g of N,N-dicyclohexylcarbodiimide and 50 mg of N,N-dimethylaminopyridine in 300 ml of methylene chloride was kept at room temperature for 4 hours.

The reaction mixture was filtered to separate the N,N-dicyclohexylurea and the solution was washed with water, dried over sodium sulfate and evaporated. The residue was taken up with 50 ml of ethyl acetate. This solution was filtered and evaporated. The residue was crystallized from ethyl ether/petroleum ether (b.p. 30°–70° C.)=1:1.

$N^5$-[2-(3-O-benzyloxy-4-O-methoxymethoxyphenyl)-ethyl]-$N^2$-benzyloxycarbonyl-L-glutamine methylester was obtained, m.p. 64°–66° C.

EXAMPLE 57

A solution of 13.5 g of $N^5$-[2-(3-O-benzyloxy-4-O-methoxymethoxyphenyl)-ethyl]-$N^2$-benzyloxycarbonyl-L-glutamine methylester obtained as described in example 56, and of 0.5 ml of concentrate hydrochloric acid in 200 ml of methanol was refluxed for 45 minutes. The reaction mixture was concentrated, diluted with methylene chloride, washed with water, dried over sodium sulfate and evaporated to dryness. The residue was crystallized from ethyl ether to give 11.5 g of $N^5$-[2-(3-benzyloxy-4-hydroxyphenyl)-ethyl]-$N^2$-benzyloxycarbonyl-L-glutamine methylester, m.p. 110°–115° C.

EXAMPLE 58

Proceeding as in example 2 but substituting for the 3-O-benzyl-N-benzyloxycarbonyldopamine an equivalent quantity of $N^5$-[2-(3-benzyloxy-4-hydroxyphenyl)-ethyl]-$N^2$-benzyloxycarbonyl-L-glutamine methylester obtained as described in example 57, and purifying the product by chromatography on a silica gel column, eluting with methylene chloride with increasing quantities up to 10% of ethyl acetate. $N^5$-[2-(3-benzyloxy-4-hydroxyphenyl)-ethyl]-$N^2$benzyloxycarbonyl-L-glutamine 4-O-dibenzylphosphate in chromatographically pure oily form (T.L.C., eluent: methylene chloride/toluene/methanol=25/10/2, UV, $I_2$ detection) was obtained.

EXAMPLE 59

Proceeding as in example 3 but replacing for the 3-O-benzyl-N-benzyloxycarbonyldopamine 4-O-dibenzylphosphate an equivalent quantity of $N^5$-[2-(3-benzyloxy-4-hydroxyphenyl)-ethyl]-$N^2$-benzyloxycarbonyl-L-glutamine 4-O-dibenzylphosphate obtained as described in example 58, $N^5$-[2-(3,4-dihydroxyphenyl)-ethyl]-L-glutamine 4-O-dihydrogenphosphate was obtained, m.p. 193°–196° C. (from water).

EXAMPLE 60

Proceeeding as in example 30 but replacing for 3-O-benzyl-N-benzyloxycarbonyl-N-methyldopamine an equivalent quantity of 3-O-benzyl-N-benzyloxycarbonyldopamine (obtained as described in example 1) and purifying the product by chromatography on silica gel column, eluting with methylene chloride/ethyl acetate/methanol=85/10/5, 3-O-benzyl-N-benzyloxycarbonyldopamine 4-O-ethylhydrogenphosphate was obtained in chromatographically pure oily form (T.L.C., eluent: n-butanol/acetic acid/acetone/water/toluene=1/1/1/1/1, UV, $I_2$ detection).

EXAMPLE 61

Proceeding as in example 3, but replacing for 3-O-benzyl-N-benzyloxycarbonyldopamine 4-O-dibenzylphosphate an equivalent quantity of 3-O-benzyl-N-benzyloxycarbonyldopamine 4-O-ethylhydrogenphosphate obtained as described in example 60, dopamine 4-O- ethyl-hydrogenphosphate was obtained, m.p. 130°–132° C. (from ethanol/water).

EXAMPLE 62

A mixture of 69.4 g of 3-benzyloxy-4-methoxybenzaldelyde, 54.5 g of sodium p-thiocresolate in 350 ml of toluene and 67 ml of hexamethylenephosphorotriamide was refluxed for 3 hours. The mixture was then poured in water and acidified. The organic phase was separated and extracted with toluene. The combined organic phase was washed with water, dried over sodium sulfate, filtered and evaporated under reduced pressure. The residue was crystallized from ethanol, thus obtained 3-benzyloxy-4-hydroxy-benzaldehyde, mp. 110°–113° C.

EXAMPLE 63

A solution of 300 g of 3-benzyloxy-4-hydroxybenzaldeyde (obtained as described in example 62) in 600 ml of dimethylformamide was added to a suspension of 34.6 g of sodium hydride in 346 ml of dimethylformamide under stirring in nitrogen atmosphere. After complete dissolution of sodium hydride 116 g of chloromethyl methyl ether were added; stirring was continued for 30 minutes. The mixture was then diluted with water and extracted with ethyl ether. The combined organic phase was dried over sodium sulfate, filtered and evaporated. The residue was distilled (b.p. 178°–183° C./0.1 mm Hg) to give 3-benzyloxy-4-methoxybenzaldehyde, m.p. 30° C. (from petroleum ether, b.p. 30°–70° C.).

EXAMPLE 64

13.5 g of acetic acid and 31 ml of 33% methylamine in ethanol were added to a solution of 282 g of 3-benzyloxy-4-methoxymethoxybenzaldeyde (obtained as described in example 63) at 0° C. At this temperature, 75.8 g of nitromethane were added and the mixture was allowed to stand at 5° C. for 4 days.

The precipitate was filtered and washed with methanol. 3-Benzyloxy-4-methoxymethoxynitrostyrene was thus obtained, m.p. 75°–76° C.

EXAMPLE 65

50 g of 3-benzyloxy-4-methoxymethoxynitrostyrene (obtained as described in example 64) in 330 ml of tetrahydrofurane were added to a suspension of 18 g of LiAlH$_4$ in 300 ml of tetrahydrofurane. After 1 hour under reflux, excess LiAlH$_4$ was decomposed with 65 ml of 40% sodium hydroxide; the salts were filtered and the filtrate was evaporated to dryness. The residue was dissolved in toluene, washed with water, dried over sodium sulfate and evaporated to dryness. Maleic acid dissolved in ethyl acetate was added to a solution of the thus obtained oil dissolved in ethyl acetate; the mixture was then heated to reflux. 3-O-Benzyl-4-O-methoxymethyldopamine maleate was precipitated by cooling, m.p. 133°–134° C.

EXAMPLE 66

A mixture of 10 g of 3-O-benzyl-4-O-methoxymethyldopamine base (prepared from the corresponding maleate obtained as described in example 65 by suspension in water, neutralization with ammonium hydroxide and extraction of the base with chloroform, drying over sodium sulfate and evaporation to dryness) and of 9.95 g of 4-benzyloxy methyl mandelate was kept at 90° C. under vacuum for 7 hours. The oil was purified by chromatography on silica gel column using methylene chloride as eluent in increasing quantities up to 20% of ethyl acetate, N-[2-(3-benzyloxy-4-methoxymethoxyphenyl)-ethyl]-4-benzyloxy-mandelamide was thus obtained, m.p. 97°–98° C. (from petroleum ether, b.p. 30°–70° C.).

EXAMPLE 67

A solution of 12 g of N-[2-(3-benzyloxy-4-methoxymethoxyphenyl)-ethyl]-4-benzyloxy-mandelamide (obtained as described in example 66) in 120 ml of methanol and 0.2 ml of concentrate hydrochloric acid was kept under reflux for 1 hour. The mixture was concentrated to one third volume; N-[2-(3-benzyloxy-4-hydroxyphenyl)-ethyl]-4-benzyloxy-mandelamide was precipitated by cooling, m.p. 137°–138° C.

EXAMPLE 68

148 ml of 1.67M boron hydride in tetrahydrofurane were added to a solution of 11.3 g of N-[2-(3-benzyloxy-4-hydroxyphenyl)-ethyl]-4-benzyloxy-mandelamide (obtained as described in example 67) in 100 ml of tetrahydrofurane. After 3 hours under reflux, the mixture was cooled and 6.93 g of propionic acid were added. The mixture was refluxed again for 1 hour and then evaporated to dryness. The resulting oil was dissolved in methylene chloride, washed with water and diluted sodium hydroxide, dried over sodium sulfate, filtered and evaporated to dryness. The residue was purified by chromatography on silica gel column using methylene chloride/methanol/ammonium hydroxide=97/3/0.3 as eluent. N-[2-(4-Benzyloxyphenyl)-2-hydroxyethyl]-3-O-benzyldopamine was thus obtained, m.p. 124°–125° C. (from ethanol).

EXAMPLE 69

2.86 g of methansulfonic acid in 10 ml of methylene chloride were added to a solution of 3.5 g of N-[2-(4-hydroxyphenyl)-2-hydroxyethyl]-3-O-benzyldopamine (obtained as described in example 68) in 140 ml of methylene chloride at 0° C. After 2 hours at the same temperature, dilute sodium bicarbonate was added; the organic phase was separated, washed with water, dried over sodium sulfate, filtered and evaporated. The residue was crystallized from ethanol, thus obtaining 7-benzyloxy-8-hydroxy-1-(4-benzyloxyphenyl)-2,3,4,5-tetrahydro-1H-3-benzoazepine, m.p. 221°–223° C.

EXAMPLE 70

A solution of 1.04 g of benzyl chlorocarbonate in 37 ml of toluene and a solution of 49 ml of 0.2N sodium hydroxide were added at the same time at 0° C. to a solution of 3.4 g of 7-benzyloxy-8-hydroxy-1-(4-benzyloxyphenyl)-2,3,4,5-tetrahydro-1H-3-benzoazepine (obtained as described in example 69) dissolved in 34 ml of toluene and 37.6 ml of 2N hydroxide. After 4 hours at the same temperature as above, toluene was separated and the aqueous phase extracted with further toluene. The combined organic phase was washed with water, dried over sodium sulfate, filtered and evaporated. The residue was purified by chromatography on a silica gel column using methylene chloride as eluent, thus obtained N-benzyloxycarbonyl-7-benzyloxy-8-hydroxy-1-(4-benzyloxyphenyl)-2,3,4,5-tetrahydro-1H-3-benzoazepine in chromatographically pure oily form (T.L.C, eluent: toluene/ethyl acetate=8/2, UV, I$_2$ detection).

EXAMPLE 71

Proceeding as in example 2 but replacing for 3-O-benzyl-N-benzyloxycarbonyldopamine an equivalent quantity of N-benzyloxycarbonyl-7-benzyloxy-8-hydroxy-1-(4-benzyloxyphenyl)-2,3,4,5-tetrahydro-1H-3-benzoazepine (obtained as described in example 70), N-benzyloxycarbonyl-7-benzyloxy-8-hydroxy-1-(4-benzyloxyphenyl)-2,3,4,5-tetrahydro-1H-3-benzoazepine 8-O-dibenzyl phosphate was obtained in chromatographically pure oily form (T.L.C., eluent: toluene/ethyl acetate=8/2, UV or $I_2$, detection).

EXAMPLE 72

Proceeding as in example 3, but replacing for 3-O-benzyl-N-benzyloxycarbonyldopamine 4-O-dibenzylphosphate an equivalent quantity of N-benzyloxycarbonyl-7-benzyloxy-8-hydroxy-1-(4-benzyloxyphenyl)-2,3,4,5-tetrahydro-1H-3-benzoazepine 8-O-dibenzylphosphate (obtained as described in example 71), 7,8-dihydroxy-1-(4-hydroxyphenyl)-2,3,4,5-tetrahydro-1H-3-benzoazepine 8-O-dihydrogenophosphate was obtained; m.p.: decomposition above 250° C. (crystallized from water).

EXAMPLE 73

Proceeding as in example 30 but replacing for 3-O-benzyl-N-benzyloxycarbonyl-N-methyldopamine an equivalent quantity of $N^5$-[2-(3-benzyloxy-4-hydroxyphenyl)ethyl]-$N^2$-benzyloxycarbonyl-L-glutamine methylester (obtained as described in example 57) and purifying the product by chromatography on silica gel column, eluting with methylene chloride with increasing quantities up to 3% methanol, $N^5$-[2-(3-benzyloxy-4-hydroxyphenyl)ethyl]-$N^2$-benzyloxycarbonyl-L-glutamine methylester 4-O-ethyl-hydrogenphosphate was obtained in chromatographically pure oily form (T.L.C., eluent: methylene chloride/methanol/water/acetic acid=79/15/1/1, UV or $I_2$ detection).

EXAMPLE 74

Proceeding as in example 3 but replacing for 3-O-benzyl-N-benzyloxycarbonyldopamine 4-O-dibenzylphosphate an equivalent quantity of $N^5$-[2-(3-benzyloxy-4-(hydroxyphenyl)ethyl]-$N^2$-benzyloxycarbonyl-L-glutamine methyl ester 4-O-ethyl-hydrogenphosphate (obtained as described in example 73), $N^5$-[2-[3-hydroxy-4-(ethyl-hydrogenphosphonoxy)phenyl]-ethyl]-L-glutamine methyl ester was obtained, m.p. 120° C. (from water/ethanol).

EXAMPLE 75

8.72 g of ethyl chloroformiate in 50 ml of methylene chloride were added to a solution of 20 g of 6-oxy-6-(2-phenylethylaminohexanoic acid and 8.15 g of triethylamine in 300 ml of methylene chloride in nitrogen atmosphere at −10° C. After 10 minutes at this temperature, 23.1 g of 3-O-benzyl-4-O-methoxymethyldopamine base (obtained as described in example 66) in 50 ml of methylene chloride were added. Temperature was allowed to rise spontaneously and the mixture was then refluxed for 20 minutes. The reaction mixture was poured in water and extracted with chloroform. The combined organic phase was dried over sodium sulfate, filtered and evaporated to dryness. The residue was crystallized from ethanol, thus obtaining N-[2-(3-benzyloxy-4-methoxymethoxyphenyl)-ethyl]-N'-(2-phenylethyl)-hexane-1-6-diamide, m.p. 141°–142° C.

EXAMPLE 76

31 ml of 10M $BH_3.(CH_3)_2S$ were added to a solution of 27 g of N-[2-(benzyloxy-4-methoxymethoxyphenyl)-ethyl]-N'-(2-phenylethylhexane-1,6-diamide (obtained as described in example 75) in 250 ml of tetrahydrofurane, in nitrogen atmosphere. The mixture was heated to reflux for 1 night and 230 ml of methanol were added after cooling. When effervescence was over, hydrochloric acid in methanol was added and the solution was refluxed for 1 hour. N-[2-(3-Benzyloxy-4-hydroxyphenyl)-ethyl]-N'-(2-phenylethyl)-heane-1,6-diamine dihydrochloride was precipitated by cooling, m.p. 249°–251° C.

EXAMPLE 77

Proceeding as in example 70, but replacing for 7-benzyloxy-8-hydroxy-1-(4-benzyloxyphenyl)-2,3,4,5-tetrahydro-1H-3-benzoazepine an equivalent quantity of N-[2-(3-benzyloxy-4-hydroxyphenyl)ethyl]-N'-(2-phenylethyl)hexane-1,6-diamine base (prepared from the corresponding hydrochloride obtained as described in example 76, by suspension in water, neutralization with ammonium hydroxide and extraction with chloroform of the base, drying over sodium sulfate and evaporation to dryness) and by doubling benzyl chlorocarbonate equivalents, N,N'-bis-(benzyloxycarbonyl)-N-[2-(3-benzyloxy-4-hydroxyphenyl)-ethyl]-N'-(2-phenylethyl)-hexane-1,6-diamine was obtained in chromatographically pure oily form (T.L.C., eluents: methylene chloride/methanol=98/2, UV, $I_2$ detection).

EXAMPLE 78

Proceeding as in example 2, but replacing for 3-O-benzyl-N-benzyloxycarbonyldopamine an equivalent quantity of N,N'-bis-(benzyloxycarbonyl)-N-[2-(3-benzyloxy-4-hydroxy-phenyl)-ethyl]-N'-(2-phenylethyl)-hexane-1,6-diamine obtained as described in example 77, N,N'-bis-(benzyloxycarbonyl)-N-[2-(3-benzyloxy-4-hydroxyphenyl)-ethyl]-N'-(2-phenylethyl)-hexane-1,6-diamine 4-O-dibenzylphosphate was obtained in chromatographically pure oily from (T.L.C., eluent: methylene chloride/ethyl acetate=9/1).

EXAMPLE 79

Proceeding as in example 3, but replacing for 3-O-benzyl-N-benzyloxycarbonyldopamine 4-O-dibenzylphosphate an equivalent quantity of N,N'-bis-(benzyloxycarbonyl)-N-[2-(3-benzyloxy-4-hydroxyphenyl)-ethyl]-N'-(2-phenylethyl)-hexane-1,6-diamine 4-O-dibenzylphosphate obtained as described in example 78, N-(3,4-dihydroxyphenylethyl)-N'-(2-phenylethyl)-hexane-1,6-diamine 4-O-dihydrogenphosphate was obtained, m.p. 220°–225° C. (from water/ethanol).

EXAMPLE 80

Proceeding as in example 70, but replacing for 7-benzyloxy-8-hydroxy-1-(4-benzyloxyphenyl)-2,3,4,5-tetrahydro-1H-3-benzoazepine an equivalent quantity of 3-O-benzyl-4-O-methoxymethyl-N[3-(4-benzyloxyphenyl)-1-methylpropyl]-dopamine base obtained as described in example 48, 3-O-benzyl-4-O-methoxymethyl-N-[3-(4-benzyloxyphenyl)-1-methylpropyl]-N-benzyloxycarbonyl-dopamine was obtained in chromatographically pure oily form (T.L.C., eluent: toluene/ethyl acetate=9/1).

EXAMPLE 81

Proceeding as in example 67, but replacing for N-[2-(3-benzyloxy-4-methoxymethoxyphenyl-ethyl]-4-benzyloxy-mandelamide an equivalent quantity of 3-O-benzyl-4-O-methoxymethyl-N-[3-(4-benzyloxyphenyl)-1-methylpropyl]-N-benzyloxycarbonyldopamine obtained as described in example 80, 3-O-benzyl-N-[3-(4-benzyloxyphenyl)-1-methylpropyl]-N-benzyloxy-carbonyldopamine was obtained, m.p. 70°–73° C.

EXAMPLE 82

Proceeding as in example 30, but replacing for 3-O-benzyl-N-benzyloxycarbonyl-N-methyldopamine an equivalent quantity of 3-O-benzyl-N-[3-(4-benzyloxyphenyl)-1-methylpropyl]-N-benzyloxycarbonyldopamine obtained as described in example 81, 3-O-benzyl-N-[3-(4-benzyloxyphenyl)-1-methylpropyl]-N-benzyloxy-carbonyl dopamine 4-O-ethyl-hydrogenphosphate was obtained, m.p. 60°–65° C. (from methylene chloride).

EXAMPLE 83

Proceeding as in example 3, but replacing for 3-O-benzyl-N-benzyloxycarbonyldopamine an equivalent quantity of 3-O-benzyl-N[3-(4-benzyloxyphenyl)-1-methypropyl]-N-benzyloxycarbonyldopamine 4-O-ethyl-hydrogenphosphate obtained as in example 82, N-[3-(4-hydroxyphenyl)-1-methylpropyl]-dopamine 4-O-ethyl-hydrogenphosphate was obtained, m.p. 188°–193° C. (from ethanol).

EXAMPLE 84

A mixture of 78 g of 2-chloro-3-hydroxy-4-methoxybenzaldehyde, 60.7 g of benzyl chloride, 3.9 g of sodium jodide, 74.6 g of potassium carbonate in 0.5 l of 95% ethanol was refluxed for 2 hours. After cooling the mixture was poured in water, the separated product was filtered and then recrystallized from absolute ethanol. 2-chloro-3-benzyloxy-4-methoxybenzaldehyde was obtained, m.p. 86°–88° C.

EXAMPLE 85

Proceeding as in example 62, but replacing for 3-benzyloxy-4-methoxybenzaldehyde an equivalent quantity of 2-chloro-3-benzyloxy-4-methoxybenzaldehyde (obtained as described in example 84) and purifying the reaction raw product by chromatography on a silica gel column, eluting with methylene chloride/petroleum ether (b.p. 30°–70° C.)=1/1, 2-chloro-3-benzyloxy-4-hydroxybenzaldehyde was obtained, m.p. 149°–150° C. (from methylene chloride/petrolum ether, b.p. 30°–70° C.=½).

EXAMPLE 86

Proceeding as in example 63, but replacing for 3-benzyloxy-4-hydroxybenzaldehyde an equivalent quantity of 2-chloro-3-benzyloxy-4-hydroxybenzaldehyde obtained as described in example 85, 2-chloro-3-benzyloxy-4-methoxymethoxybenzaldehyde was obtained, m.p. 66°–67° C. (from petroleum ether, b.p. 30°–70° C.).

EXAMPLE 87

0.96 g of acetic acid and 1.47 ml of a 33% w/v solution of methylamine in ethanol were added at 0° C. to a solution of 2-chloro-3-benzyloxy-4-methoxymethoxybenzaldehyde (obtained as described in example 86) in 70 ml of methylene chloride and 70 ml of methanol. 5.42 of nitromethane were then added. The mixture was kept under reflux for 22 hours and then evaporated to half volume to remove methylene chloride; 2-chloro-3-benzyloxy-4-methoxymethoxynitrostyrene was precipitated by cooling, m.p. 91°–92° C.

EXAMPLE 88

Proceeding as in example 65, but replacing for 3-benzyloxy-4-methoxymethoxynitrostyrene an equivalent quantity of 2-chloro-3-benzyloxy-4-methoxymethoxynitrostyrene obtained as described in example 87, 2-chloro-3-O-benzyl-4-O-methoxymethyl-dopamine maleate was obtained, m.p. 105°–107° C. (from ethyl acetate).

EXAMPLE 89

Proceeding as in example 66, but replacing for 3-O-benzyl-4-O-methoxymethyldopamine base an equivalent quantity of 2-chloro-3-O-methoxymethyldopamine base obtained from the corresponding maleate described in example 88, N-[2-(2-chloro-3-benzyloxy-4-methoxymethoxyphenyl)-ethyl]-4-benzyloxy-mandelamide was obtained in chromatographically pure oily form (T.L.C., eluent: toluene/ethyl acetate=1/1, UV, I$_2$ detection).

EXAMPLE 90

Proceeding as in example 67, but replacing for N-[2-(3-benzyloxy-4-methoxymethoxyphenyl)-ethyl]-4-benzyloxy-mandelamide an equivalent quantity of N-2-(2-chloro-3-benzyloxy-4-methoxymethoxyphenyl)-ethyl-4-benzyloxy-mandelamide obtained as described in example 89, N-[2-(2-chloro-3-benzyloxy-4-hydroxyphenyl)-ethyl]-4-benzyloxy-mandelamide was obtained, m.p. 136°–138° C. (from petroleum ether, b.p. 30°–70° C.).

EXAMPLE 91

Proceeding as in example 68, but replacing for N-[2-(3-benzyloxy-4-hydroxyphenyl)-ethyl]-4-benzyloxy-mandelamide an equivalent quantity of N-[2-(2-chloro-3-benzyloxy-4-hydroxyphenyl)-ethyl]-4-benzyloxy-mandelamide obtained as described in example 90, N-[2-(4-benzyloxyphenyl)-2-hydroxyethyl]-2-chloro-3-O-benzyldopamide was obtained, m.p. 139°–141° C. (from ethanol).

EXAMPLE 92

Proceeding as in example 70, but replacing for 7-benzyloxy-8-hydroxy-1-(4-benzyloxyphenyl)-2,3,4,5-tetrahydro-1H-3-benzoazepine an equivalent quantity of N-[2-(4-benzyloxyphenyl-2-hydroxyethyl]-2-chloro-3-O-benzyldopamine obtained as described in example 91, and purifying the resulting product by chromatography on silica gel column (eluent: methylene chloride/ethyl acetate=95/5), N-benzyloxycarbonyl-N-[2-(4-benzyloxyphenyl)-2-hydroxyethyl]-2-chloro-3-O-benzyl-dopamine was obtained in oily form (T.L.C., eluent: toluene/ethyl acetate=7/3, UV, I$_2$ detection).

EXAMPLE 93

Proceeding as in example 69, but replacing for N-[2-(4-hydroxyphenyl)-2-hydroxyethyl]-3-O-benzyldopamine an equivalent quantity of N-benzyloxycarbonyl-N-[2-(4-benzyloxyphenyl)-2-hydroxyethyl]-2-chloro-3-O-benzyldopamine obtained as described in example 92, N-benzyloxycarbonyl-7-benzyloxy-8-hydroxy-6-chloro-1-(4-benzyloxyphenyl)-2,3,4,5-tetrahydro-1H-3- benzoazepine was obtained in chromatographically pure oily form (T.L.C., eluent: toluene/ethyl acetate=8/2, UV, $I_2$ detection).

EXAMPLE 94

Proceeding as in example 2, but replacing for 3-O-benzyl-N-benzyloxycarbonyldopamine an equivalent quantity of N-benzyloxycarbonyl-7-benzyloxy-8-hydroxy-6-chloro-1-(4-benzyloxyphenyl)-2,3,4,5-tetrahydro-1H-3-benzoazepine obtained as described in example 93, N-benzyloxycarbonyl-7-benzyloxy-8-hydroxy-6-chloro-1-(4-benzyloxyphenyl)-2,3,4,5-tetrahydro-1H-3-benzoazepine 8-O-dibenzylphosphate was obtained in chromatographically pure oily form (T.L.C., eluent: toluene/ethyl acetate=8/2, UV, $I_2$ detection).

EXAMPLE 95

Proceeding as in example 3, but replacing for 3-O-benzyl-N-benzyloxycarbonyl dopamine 4-O-dibenzyl-phosphate an equivalent quantity of N-benzyloxycarbonyl-7-benzyloxy-8-hydroxy-6-chloro-1-(4-benzyloxyphenyl)-2,3,4,5,-tetrahydro-1H-3-benzoazepine 8-O-dibenzylphosphate (obtained as described in example 94), and for 10% Pd/C an equivalent quantity of 10% Pt/C catalyst, 7.8-dihydroxy-6-chloro-1-(4-hydroxyphenyl)-2,3,4,5-tetrahydro-1H-benzoazepine 8-O-dihydrogenphosphate (crystallized from water; m.p.: decomposition above 250° C.) was obtained.

EXAMPLE 96

Proceeding as in example 30, but replacing for 3-O-benzyl-N-benzyloxycarbonyldopamine, an equivalent quantity of N,N'-bis-(benzyloxycarbonyl)-N-[2-(3-benzyloxy-4-hydroxyphenyl)-ethyl]N'-(2-phenylethyl)-hexane-1,6-diamine obtained as described in example 77, N,N'-bis-(benzyloxycarbonyl)-N-[2-(3-benzyloxy-4-hydroxyphenyl)-ethyl]-N'-(2-phenylethyl)-hexane-1,6-diamine 4-O-ethyl-hydrogenphosphate in chromatographically pure oily form (T.L.C., eluent: methylene chloride/methanol=85/15 UV, $I_2$ detection) was obtained.

EXAMPLE 97

Proceeding as in example 3, but replacing for 3-O-benzyl-N-benzyloxycarbonyldopamine 4-O-dibenzyl-phosphate, an equivalent quantity of N,N'-bis-(benzyloxycarbonyl)-N-[2-(3-benzyloxy-4-hydroxyphenyl)ethyl]-N'-(2-phenylethyl)-hexane-1,6-diamine 4-O-ethyl-hydrogenophosphate obtained as described in example 96, N-(3.4-dihydroxyphenylethyl)-N'-(2-phenylethyl)-hexane-1,6-diamine 4-O-ethyl-hydrogenphosphate was obtained; m.p. 136°–139° C. (from ethanol/ethyl ether).

EXAMPLE 98

Proceeding as in example 22, but replacing for N-methyldopamine hydrochloride an equivalent quantity of 1-(N,N-di-n-propylaminomethyl)-5,6-dihydroxy-1,2,3,4-tetrahydro-1-naphtalenone, the two isomeric 1-(N,N-di-n-propylaminomethyl)-5,6-dihydroxy-1,2,3,4-tetrahydro-1-naphtalenone-5-O- and 6-O-dihydrogenphosphate were obtained and separated by chromatography on IRA 400 ion exchange resin.

EXAMPLE 99

Multiple dose vials of dopamine 4-O-ethyl-hydrogenphosphate, containing 5 mg/ml of active compound were prepared as follows: 100 g of dopamine 4-O-ethyl-hydrogenphosphate sodium salt, 160 g of sodium chloride and 10 g of sodium metabisulfite were dissolved in distilled water to a volume of 20 l; the solution was filtered through a sterilizing membrane (e.g. Millipore HAWP 0.22μ) and then distributed in sterile conditions in multiple-dose vials each containing 10 ml, equipped with a rubber closer under an aluminum seal. This solution is used by direct intravenous injection or by dilution in saline or glucose solution for continuous intravenous infusion and is administered at appropriate doses, e.g. 1 ml by slow intravenous injection, or by dilution in isotonic saline for continous intravenous perfusion at a rate of 1–5 μg/kg. min to patients suffering from acute cardiac and/or renal failure.

EXAMPLE 100

Film coating tablets containing 50 mg of N,N-di-n-propydopamine 4-O-dihydrogen phosphate were prepared as follows: 1000 g of the active compound were mixed in a cube blender with 890 g of microcrystalline cellulose (Avicel pH 102); the mixture was wet-granulated wetting with 30 g of polyvinylpyrrolidone dissolved in a small amount of water, mixing and pressing through a 6-mesh screen. The granules were dried in an infrared oven, added with 60 g of cross-linked polyvinylpyrrolidone and 20 g of hydrogenated castor oil, mixed in a cube blender, passed through a 20 mesh screen and then compressed with 6 mm concave punches in tablets weighing 100 mg. The tablets were then coated in a coating pan by spraying with an aqueous solution of hydroxypropylmethylcellulose (Methocel E5) and polyethylenglicol 6000 in 4:1 ratio while passing a stream of warm air until the weight of the tablets reached 103 mg. One tablet is administered to adult hypertensive patients from one to four times a day.

EXAMPLE 101

.An ophthalmic solution of dl-adrenaline 3-O-ethyl-hydrogen phosphate were be prepared as follows: 10 g of the active compound, 7.7 g of citric acid monohydrate, 15.2 g of disodium hydrogen phosphate dodecahydrate, 5 g of sodium chloride, 1 g of sodium metabisulphite and 0.1 g of benzalconium chloride were dissolved in 1.8 l of distilled water; the pH of the solution was checked and if required, adjusted to pH 6 by addition of a small amount of sodium hydroxide or phosphoric acid solution. The solution was brought to 2 l volume with distilled water, then filtered through a sterilizing membrane (e.g. Millipore HAWP 0.22μ) and filled in sterile conditions in 5 ml plastic eye-drop dispensing bottles suitable for direct instillation. The ophthalmic solutions is usefully instilled two-three times a day (1–2 drops per eye) to patients suffering from glaucoma.

EXAMPLE 102

Tablets containing 25 mg N-methyldopamine 4-O-ethyl-hydrogen phosphate were prepared as follows:

250 g of active compound were mixed with 1720 g of microcristalline cellulose (Avicel pH 102) in a cube blnder, then sieved through a 200 mesh screen and pre-compressed in slugs using 20 mm punches; the slugs were comminuted by pressing through a 16 mesh screen. The granules were blended with 30 g of magnesium stearate, sieved through the same screen and then compressed with 8 mm punches in tablets weighing 200 mg. One-two tablets are administered from one to three times a day to adult patients suffering from chronic congestive heart failure, acute and chronic renal failure or hypertension.

What is claimed is:

1. A method for improving the absorption and therefore effectiveness of a catecholamine compound in a patient exhibiting a syndrome for which the pharmacological action of said cathecholamine compound is useful, comprising converting such catecholamine compound to a mono O-phosphate ester derivative thereof, and administering to the patient an effective amount of the resulting mono O-phosphate ester derivative or of a pharmaceutically acceptable salt thereof.

2. A method as in claim 1, in which the effective amount of the mono O-phosphate ester derivative ranges from 0.01 to 10 mg/kg/day.

3. A method as in claim 1, in which either phenol hydroxy group of the catechol moiety is converted to a group of formula:

$$RO-\underset{\underset{OH}{|}}{\overset{\overset{O}{\|}}{P}}-O-$$

where

R is hydrogen, phenyl, phenylalkyl, or a $C_1$–$C_6$ alkyl optionally substituted by hydroxy, alkoxy, acyloxy, amino, carboxy or alkoxycarbonyl; or a pharmaceutically acceptable salt thereof.

4. A method as in claim 2, in which either phenol hydroxy group of the catechol moiety is converted to a group of formula:

$$RO-\underset{\underset{OH}{|}}{\overset{\overset{O}{\|}}{P}}-O-$$

where

R is hydrogen, phenyl, phenylalkyl, or a $C_1$–$C_6$ alkyl optionally substituted by hydroxy, alkoxy, acyloxy, amino, carboxy or alkoxycarbonyl; or a pharmaceutically acceptable salt thereof.

5. A method as in claim 3, in which R is hydrogen, or a $C_1$–$C_4$ alkyl optionally substituted by $C_1$–$C_4$ alkoxy or acyloxy where the acyl group is in turn an alkylcarbonyl group having from 1 to 4 carbon atoms in the alkyl moiety.

6. A method as in claim 4, in which R is hydrogen, or a $C_1$–$C_4$ alkyl optionally substituted by $C_1$–$C_4$ alkoxy or acyloxy where the acyl group is in turn an alkylcarbonyl group having from 1 to 4 carbon atoms in the alkyl moiety.

7. A method as in any one of claim 1 or 2, in which the mono O-phosphate ester derivative has the following formula:

$$\text{(I)}$$

wherein

R' is hydrogen when R" is $$RO-\underset{\underset{OH}{|}}{\overset{\overset{O}{\|}}{P}}-$$

and is $$RO-\underset{\underset{OH}{|}}{\overset{\overset{O}{\|}}{P}}-$$

when R" is hydrogen;

R is hydrogen, phenyl, phenylalkyl, or a $C_1$–$C_6$ alkyl optionally substituted by hydroxy, alkoxy, acyloxy, amino, or alkoxycarbonyl;

$R_1$ is hydrogen, halogen, alkyl, alkoxy or together with $R_3$, $R_5$ or $R_7$ has the meanings indicated below;

X is hydrogen or together with $R_3$, $R_5$ or $R_7$ has the meanings indicated below;

$R_2$ is hydrogen or hydroxy;

$R_3$ is hydrogen or together with $R_1$ or X forms a ring having from 5 to 8 members;

$R_4$ is hydrogen or alkyl;

$R_5$ is hydrogen, alkyl or together with $R_1$ or X forms a ring having from 5 to 8 members;

$R_6$ is hydrogen, allyl, an acyl group of a natural aminoacid, or a $C_1$–$C_6$ alkyl optionally substituted by phenyl, 4-hydroxy-phenyl, or by a phenylalkylamino group having from 1 to 3 carbon atoms in the alkyl moiety; $R_7$ is hydrogen, a $C_1$–$C_6$ alkyl, or together with $R_1$ or X forms a ring having from 5 to 8 members.

8. A method as in any one of claim 1 or 2, in which the mono O-phosphate ester derivative has the following formula:

$$\text{(I)}$$

wherein

R' is hydrogen when R" is $$RO-\underset{\underset{OH}{|}}{\overset{\overset{O}{\|}}{P}}-$$

and is $$RO-\underset{\underset{OH}{|}}{\overset{\overset{O}{\|}}{P}}-$$

when R" is hydrogen;

R is hydrogen, or a $C_1$–$C_4$ alkyl optionally substituted by $C_1$–$C_4$ alkoxy or acyloxy where the acyl group is in turn an alkylcarbonyl having from 1 to 4 Carbon atoms in the alkyl moiety;

$R_1$ is hydrogen, halogen or together with $R_3$, $R_5$ or $R_7$ has the meanings indicated below;

X is hydrogen or together with $R_3$, $R_5$ or $R_7$ has the meanings indicated below;

$R_2$ is hydrogen or hydroxy;

$R_3$ is hydrogen or together with $R_1$ or X trimethylene;

$R_4$ is hydrogen or methyl;

$R_5$ is hydrogen or together with $R_1$ or X ethylene;

$R_6$ is hydrogen, glutamyl, or a $C_1$–$C_6$ alkyl optionally substituted by 4-hydroxyphenyl, or by a phenylalkylamino group having from 1 to 3 carbon atoms in the alkyl moiety;

$R_7$ is hydrogen, $C_1$–$C_4$ alkyl or together with $R_1$ or X methylene, $CH_2O$, or ethylene optionally substituted by phenyl, hydroxyphenyl or trimethoxybenzyl.

9. A cathecholamine compound wherein either phenol hydroxy group of the catechol moiety has been converted to a group of formula:

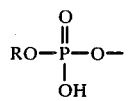

where
R is hydrogen, phenyl, phenylalkyl, or a $C_1$–$C_6$ alkyl optionally substituted by hydroxy, alkoxy, acyloxy, amino, carboxy or alkoxycarbonyl; or a pharmaceutically acceptable salt thereof.

10. A catecholamine compound as in claim 9, in which R is hydrogen, or a $C_1$–$C_4$ alkyl optionally substituted by $C_1$–$C_4$ alkoxy or acyloxy where the acyl group is in turn an alkylcarbonyl group having from 1 to 4 carbon atoms in the alkyl moiety.

11. A catecholamine compound as in claim 9, which has the following formula:

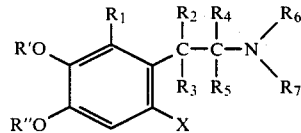

wherein
R' is hydrogen when R'' is

and is

when R'' is hydrogen,

R has the above mentioned meanings, $R_1$ is hydrogen, halogen, alkyl, alkoxy or together with $R_3$, $R_5$ or $R_7$ has the meanings indicated below;

X is hydrogen or together with $R_3$, $R_5$ or $R_7$ has the meanings indicated below;

$R_2$ is hydrogen or hydroxy;

$R_3$ is hydrogen or together with $R_1$ or X forms a ring having from 5 to 8 members;

$R_4$ is hydrogen or alkyl;

$R_5$ is hydrogen, alkyl or together with $R_1$ or X forms a ring having from 5 to 8 members;

$R_6$ is hydrogen, allyl, an acyl group of a natural aminoacid, or a $C_1$–$C_6$ alkyl optionally substituted by phenyl, 4-hydroxyphenyl or by a phenylalkylamino group having from 1 to 3 Carbon atoms in the alkyl moiety;

$R_7$ is hydrogen, a $C_1$–$C_6$ alkyl, or together with $R_1$ or X forms a ring having from 5 to 8 members.

12. A compound of formula (I) as in claim 11, wherein R is hydrogen, or a $C_1$–$C_4$ alkyl optionally substituted by $C_1$–$C_4$ alkoxy or acyloxy where the acyl group is in turn an alkylcarbonyl having from 1 to 4 Carbon atoms in the alkyl moiety; $R_1$ is hydrogen, halogen or together with $R_3$, $R_5$ or $R_7$ has the meanings indicated below; X is hydrogen or together with $R_3$, $R_5$ or $R_7$ has the meanings indicated below; $R_2$ is hydrogen or hydroxy; $R_3$ is hydrogen or together with $R_1$ or X trimethylene; $R_4$ is hydrogen or methyl; $R_5$ is hydrogen or together with $R_1$ or X ethylene; $R_6$ is hydrogen, glutamyl or a $C_1$–$C_6$ alkyl optionally substituted with 4-hydroxyphenyl, or by a phenylalkylamino having from 1 to 3 carbon atoms in the alkyl moiety; $R_7$ is hydrogen, $C_1$–$C_4$ alkyl or together with $R_1$ or X methylene, $CH_2O$, or ethylene optionally substituted by phenyl, hydroxyphenyl or trimethoxybenzyl.

13. A compound selected from the group consisting of dopamine 4-O-dihydrogenphosphate, dopamine 3-O-dihydrogenphosphate, N-methyldopamine 4-O-dihydrogenphosphate, N-methyldopamine 3-O-dihydrogenphosphate, adrenaline 3-O-dihydrogenphosphate, adrenaline 4-O-dihydrogenphosphate, 7,8-dihydroxy-1-phenyl-2,3,4,5-tetrahydro-1H-3-benzoazepine 7-O-dihydrogen phosphate, 7,8-dihydroxy-1-phenyl-2,3,4,5-tetrahydro-1H-3-benzoazepine 8-O-dihydrogen phosphate, N-methyldopamine 4-O-ethyl hydrogenphosphate, N-methyldopamina 3-O-(2-methoxy)ethyl hydrogenphosphate, N-methyldopamine 3-O-pivaloyloxymethyl hydrogenphosphate, N,N-di-n-propyldopamine 4-O-dihydrogenphosphate, N-tert.butylamino-2-(3-4-dihydroxyphenyl)-2-hydroxy-ethylamine 3-O-dihydrogenphosphate, N-[3-(4-hydroxy-phenyl)-1-methylpropyl]-dopamine 4-O-dihydrogenphosphate, 1-(3,4,5-trimethoxybenzyl)-6,7-dihydroxy-1,2,3,4-tetrahydroisoquinoline 7-O-dihydrogenphosphate, $N^5$-[2-(3,4-dihydroxyphenyl)-ethyl]-L-glutamine 4-O-dihydrogen phosphate, dopamine 4-O-ethyl-hydrogenphosphate, 7,8-dihydroxy-1-(4-hydroxyphenyl)-2,3,4,5-tetrahydro-1H-3-benzoazepine 8-O-dihydrogenphosphate, $N^5$-[2-(3-hydroxy-4-(ethyl-hydrogenphosphonoxy)-phenyl)-ethyl]-L-glutamine methylester 4-O-ethylhydrogen phosphate, N-(3,4-dihydroxyphenylethyl)-N'-(2-phenylethyl)-hexane-1,6-dihydrogenphosphate, N-[3-(4-hydroxyphenyl)-1-methylpropyl]-dopamine 4-O-ethyl hydrogenphosphate, 7,8-dihydroxy-6-chloro-1-(4-hydroxyphenyl)-2,3,4,5-tetrahydro-1H-3-benzoazepine 8-O-dihydrogenphosphate, N-(3,4-dihydrophenylethyl)-N'-(2-phenylethyl)-hexane-1,6-diammine 4-O-ethyl-hydrogenphosphate, 1-(N,N-di-n-propylaminomethyl)-5,6-dihydroxy-1,2,3,4-tetrahydro-1-naphthalene 5-O-dihydrogenphosphate, 1-(N,N-di-n-propylaminomethyl)-5-6-dihydroxy-1,2,3,4-tetrahydro-1-naphtalene 6-O-dihydrogenphosphate, and a pharmaceutically acceptable salt thereof.

14. A pharmaceutical composition comprising an effective amount of a catecholamine compound according to claim 9 or of a pharmaceutically acceptable salt thereof together with a pharmaceutically acceptable carrier.

15. A pharmaceutical composition comprising an effective amount of a catecholamine compound according to claim 10 or of a pharmaceutically acceptable salt thereof together with a pharmaceutically acceptable carrier.

16. A pharmaceutical composition comprising an effective amount of a catecholamine compound according to claim 11 or of a pharmaceutically acceptable salt thereof together with a pharmaceutically acceptable carrier.

17. A pharmaceutical composition comprising an effective amount of a catecholamine compound according to claim 12 or of a pharmaceutically acceptable salt thereof together with a pharmaceutically acceptable carrier.

18. A pharmaceutical composition comprising an effective amount of a catecholamine compound according to claim 13 or of a pharmaceutically acceptable salt thereof together with a pharmaceutically acceptable carrier.

19. A method of improving absorption of a catecholamine which comprises converting either phenol hydroxy group thereof to a mono O-phosphate ester derivative thereof.

20. In a method which comprises administering an effective amount of a catecholamine to patient in need of catecholamine therapy, the improvement wherein the catecholamine is in the form of a pharmaceutically-acceptable mono O-phosphate ester derivative or of a pharmaceutically-acceptable salt thereof.

* * * * *